US012029804B2

(12) United States Patent
Song

(10) Patent No.: US 12,029,804 B2
(45) Date of Patent: Jul. 9, 2024

(54) PEPTIDE FOR PROMOTING MUCOUS MEMBRANE PERMEATION AND COMPOSITION CONTAINING SAME

(71) Applicant: SOONCHUNHYANG UNIVERSITY INDUSTRY ACADEMY COOPERATION FOUNDATION, Asan-si (KR)

(72) Inventor: Keon Hyoung Song, Asan-si (KR)

(73) Assignee: SOONCHUNHYANG UNIVERSITY INDUSTRY ACADEMY COOPERATION FOUNDATION, Chungcheongnam-Do (KR)

( * ) Notice: Subject to any disclaimer, the term of this patent is extended or adjusted under 35 U.S.C. 154(b) by 422 days.

(21) Appl. No.: 17/290,565

(22) PCT Filed: Nov. 1, 2019

(86) PCT No.: PCT/KR2019/014761
§ 371 (c)(1),
(2) Date: Jul. 15, 2021

(87) PCT Pub. No.: WO2020/091535
PCT Pub. Date: May 7, 2020

(65) Prior Publication Data
US 2021/0401718 A1 Dec. 30, 2021

(30) Foreign Application Priority Data
Nov. 2, 2018 (KR) .................. 10-2018-0133851

(51) Int. Cl.
*A61K 8/64* (2006.01)
(52) U.S. Cl.
CPC ..................... *A61K 8/64* (2013.01)

(58) Field of Classification Search
CPC ........ A61K 8/64; A61K 38/08; A61K 9/0043; A61K 9/00; C07K 7/06
See application file for complete search history.

(56) References Cited

U.S. PATENT DOCUMENTS 10,307,458 B2 * 6/2019 Song .................. C07K 7/06
2002/0042097 A1 4/2002 Tirrell et al.
(Continued)

FOREIGN PATENT DOCUMENTS

EP 3 162 811 A1 5/2017
KR 10-2007-0117551 12/2007
(Continued)

OTHER PUBLICATIONS

Gundogdu et al. "Assessment of fexofanadine hydrochloride permeability and dissolution with an anionic surfactant using Caco-2 cells" in Pharmazie, 66:747-753 (2011), (Year: 2011).*
(Continued)

*Primary Examiner* — Blessing M Fubara
(74) *Attorney, Agent, or Firm* — NIXON & VANDERHYE, PC

(57) ABSTRACT

A peptide and a peptide multimer according to the present invention serve to control tight bonding between cells, and thereby facilitate the absorption, through a mucous membrane, of an active ingredient of co-administered drugs and the like. Thus, the bioavailability of the active ingredient can be significantly improved, and as a result, the therapeutic effect of the active ingredient can be significantly improved.

9 Claims, 3 Drawing Sheets

Specification includes a Sequence Listing.

(56) References Cited

U.S. PATENT DOCUMENTS

| | | | |
|---|---|---|---|
| 2007/0196272 A1 | 8/2007 | Eddington et al. | |
| 2008/0014218 A1 | 1/2008 | Fasano et al. | |
| 2011/0117106 A1* | 5/2011 | Prince | A61P 11/06 |
| | | | 514/471 |
| 2017/0143785 A1* | 5/2017 | Song | A61K 38/08 |

FOREIGN PATENT DOCUMENTS

| | | |
|---|---|---|
| KR | 10-2014-0056396 | 5/2014 |
| KR | 10-1470793 | 12/2014 |
| KR | 10-2017-0138861 | 12/2017 |
| WO | 2006/076587 | 7/2006 |
| WO | 2007/095091 | 8/2007 |
| WO | 2007/134241 | 11/2007 |
| WO | 2008/060552 | 5/2008 |
| WO | 2015/038662 | 3/2015 |

OTHER PUBLICATIONS

Oliver Demmer, et al., "Design, Synthesis, and Functionalization of Dimeric Peptides Targeting Chemokine Receptor CXCR4", Journal of Medicinal Chemistry, vol. 54, published Sep. 12, 2011, pp. 7648-7662 (15 pages).

Simeon E. Goldblum, et al., "The active Zot domain (aa 288-293) increases ZO-1 and myosin 1C serine/threonine phosphorylation, alters interaction between ZO-1 and its binding partners, and induces tight junction disassembly through proteinase activated receptor 2 activation", The FASEB Journal, 2011, vol. 25, 144-158 (15 pages).

Peter W. Schiller, et al., "Synthesis and Activity Profiles of Novel Cyclic Opioid Peptide Monomers and Dimers", Journal of Medicinal Chemistry, vol. 28, No. 12, 1985, pp. 1766-1771 (6 pages).

Keon-Hyoung Song, et al., "Effect of the six-mer synthetic peptide (AT1002) fragment of zonula occludens toxin on the intestinal absorption of cyclosporin A", International Journal of Pharmaceutics, vol. 351, 2008, pp. 8-14 (7 pages).

Keon-Hyoung Song, et al., "The Impact of AT1002 on the Delivery of Ritonavir in the Presence of Bioadhesive Polymer, Carrageenan", Archives of Pharmacal Research, vol. 35, No. 5, 2012, pp. 937-943 (7 pages).

Keon-Hyoung Song, et al., "The Influence of Stabilizer and Bioadhesive Polymer on the Permeation-Enhancing Effect of AT1002 in the Nasal Delivery of a Paracellular Marker", Archives of Pharmacal Research, vol. 35, No. 2, 2012, pp. 359-366 (8 pages).

Keon-Hyoung Song, et al., "Paracellular permeation-enhancing effect of AT1002 C-terminal amidation in nasal delivery", Drug Design, Development and Therapy, vol. 9, 2015, pp. 1815-1823 (9 pages).

Grant of Patent for KR Application No. 10-2019-0138751 dated Jul. 1, 2020, 4 pages (with English Translation).

Notification of Reason for Refusal for KR Application No. 10-2019-0138751 dated Apr. 18, 2020, 8 pages (with English Translation).

International Search Report for PCT/KR2019/014761 dated Feb. 20, 2020, 10 pages.

Partial Supplementary European Search Report for corresponding European Application No. 19880686.1 dated Jul. 11, 2022, 24 pages.

Li, M. et al., "Structure-activity relationship studies of permeability modulating peptide AT-1002", Bioorganic & Medicinal Chemistry Letters, Elsevier, Amsterdam, NL, vol. 18, No. 16, Aug. 15, 2008, pp. 4584-4586, XP023613426.

* cited by examiner

SEQUENCE LISTING

<160> NUMBER OF SEQ ID NOS: 15

<210> SEQ ID NO 1
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (2)
<223> OTHER INFORMATION: Xaa is 3-Azidoalanine

<400> SEQUENCE: 1

Phe Xaa Ile Gly Arg Leu
1               5

<210> SEQ ID NO 2
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (1)
<223> OTHER INFORMATION: Xaa can be Ala Val Leu Ile Pro Trp Tyr or Met
<220> FEATURE:
<221> NAME/KEY: PEPTIDE
<222> LOCATION: (2)
<223> OTHER INFORMATION: Xaa is 3-Azidoalanine

<400> SEQUENCE: 2

Xaa Xaa Ile Gly Arg Leu
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (2)
<223> OTHER INFORMATION: Xaa is 3-Azidoalanine
<220> FEATURE:
<221> NAME/KEY: PEPTIDE
<222> LOCATION: (3)
<223> OTHER INFORMATION: Xaa can be Ala Val Leu Pro Trp or Met

<400> SEQUENCE: 3

Phe Xaa Xaa Gly Arg Leu
1               5

<210> SEQ ID NO 4
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (2)
<223> OTHER INFORMATION: Xaa is 3-Azidoalanine
<220> FEATURE:
<221> NAME/KEY: PEPTIDE
<222> LOCATION: (4)
<223> OTHER INFORMATION: Xaa can be Ser Thr Tyr Asn Ala or Gln

<400> SEQUENCE: 4

```
Phe Xaa Ile Xaa Arg Leu
1               5

<210> SEQ ID NO 5
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (2)
<223> OTHER INFORMATION: Xaa is 3-Azidoalanine
<220> FEATURE:
<221> NAME/KEY: PEPTIDE
<222> LOCATION: (5)
<223> OTHER INFORMATION: Xaa can be Lys or His

<400> SEQUENCE: 5

Phe Xaa Ile Gly Xaa Leu
1               5

<210> SEQ ID NO 6
<211> LENGTH: 6
<212> TYPE: PRT
<213> ORGANISM: Artificial Sequence
<220> FEATURE:
<223> OTHER INFORMATION: synthetic peptide

<400> SEQUENCE: 6

Phe Cys Ile Gly Arg Leu
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (1)
<223> OTHER INFORMATION: Xaa can be Ala Val Leu Ile Pro Trp Tyr or Met

<400> SEQUENCE: 7

Xaa Cys Ile Gly Arg Leu
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (2)
<223> OTHER INFORMATION: Xaa can be Gly Ser Thr Tyr Asn or Gln

<400> SEQUENCE: 8

Phe Xaa Ile Gly Arg Leu
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic peptide
<220> FEATURE:
```

```
<221> NAME/KEY: PEPTIDE
<222> LOCATION: (3)
<223> OTHER INFORMATION: Xaa can be Ala Val Leu Pro Trp or Met

<400> SEQUENCE: 9

Phe Cys Xaa Gly Arg Leu
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (4)
<223> OTHER INFORMATION: Xaa can be Ser Thr Tyr Asn Ala or Gln

<400> SEQUENCE: 10

Phe Cys Ile Xaa Arg Leu
1               5

<210> SEQ ID NO 11
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (5)
<223> OTHER INFORMATION: Xaa can be Lys or His

<400> SEQUENCE: 11

Phe Cys Ile Gly Xaa Leu
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (2)
<223> OTHER INFORMATION: Xaa is 3-Azidoalanine
<220> FEATURE:
<221> NAME/KEY: PEPTIDE
<222> LOCATION: (6)
<223> OTHER INFORMATION: Xaa is a variant of leucine wherein the
      carboxyl group -COOH is modified to -CONH2

<400> SEQUENCE: 12

Phe Xaa Ile Gly Arg Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (6)
<223> OTHER INFORMATION: Xaa is a variant of leucine wherein the
      carboxyl group -COOH is modified to -CONH2

<400> SEQUENCE: 13
```

-continued

```
Phe Cys Ile Gly Arg Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (1)
<223> OTHER INFORMATION: Xaa is 3-Azidoalanine

<400> SEQUENCE: 14

Xaa Phe Cys Ile Gly Arg Leu
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: PEPTIDE
<222> LOCATION: (1)
<223> OTHER INFORMATION: Xaa is 3-Azidoalanine
<220> FEATURE:
<221> NAME/KEY: PEPTIDE
<222> LOCATION: (7)
<223> OTHER INFORMATION: Xaa is a variant of leucine wherein the
      carboxyl group -COOH is modified to -CONH2

<400> SEQUENCE: 15

Xaa Phe Cys Ile Gly Arg Xaa
1               5
```

PEPTIDE FOR PROMOTING MUCOUS MEMBRANE PERMEATION AND COMPOSITION CONTAINING SAME

This application is the U.S. national phase of International Application No. PCT/KR2019/014761 filed Nov. 1, 2019 which designated the U.S. and claims priority to Korean Patent Application No. 10-2018-0133851 filed Nov. 2, 2018, the entire contents of each of which are hereby incorporated by reference.

TECHNICAL FIELD

The present invention relates to a peptide for promoting mucous membrane permeation, a peptide multimer, and a composition or a formulation containing same.

BACKGROUND

Despite excellent efficacy, drugs with low bioavailability are not easy to exert their efficacy when orally administered to the human body. Accordingly, various efforts have been made to improve the bioavailability of drugs, and in particular, many attempts have been made to promote the absorption of drugs through mucous membrane such as small intestine, nasal mucous membrane, and the like when orally or nasally administered.

The absorption of drugs into the body is performed in such a way that the drugs pass through the mucous membrane and flow through the blood circulation system of the body. Such absorption of drugs is not easily performed mainly due to a tight junction between the cells which form the mucous membrane. This is because the tight junction plays a role of sealing between the cells, in which a plasma membrane is tightly closed between neighboring cells, so that water-soluble molecules cannot easily leak through an intercellular space, thereby limiting the movement of substances between the cells.

Thus, there is a need to develop a method and a substance capable of increasing the absorption of drugs into the body without cytotoxicity when administered together with drugs by controlling the tight junction in the body.

PRIOR ART DOCUMENTS

Patent Document (Patent Document 1) WO 07/095091
(Patent Document 2) WO 07/134241

Non-Patent Document (Non-Patent Document 1) International Journal of Pharmaceutics 351 (2008) 8-14
(Non-Patent Document 2) Arch Pharm Res Vol 35, No 5, 937-943, 2012
(Non-Patent Document 3) Arch Pharm Res Vol 35, No 2, 359-366, 2012

DETAILED DESCRIPTION OF THE INVENTION

Technical Problem

The present invention provides a composition for promoting mucous membrane permeation comprising a peptide or a peptide multimer for increasing the absorption of active ingredients into the body.

The present invention provides a formulation comprising a peptide or a peptide multimer for increasing the absorption of active ingredients into the body, and the active ingredients.

The present invention provides a cosmetic composition comprising a peptide or a peptide multimer for increasing the absorption of active ingredients into the body.

The present invention provides a use of a peptide or a peptide multimer for promoting mucous membrane permeation of active ingredients.

The present invention provides a method for promoting mucous membrane permeation of active ingredients, comprising a step of administering a peptide or a peptide multimer into a subject.

The present invention provides a use of a peptide or a peptide multimer in the manufacture of a medicament for promoting mucous membrane permeation of active ingredients.

Technical Solution

The present invention provides a composition for promoting mucous membrane permeation including at least one peptide selected from the group consisting of: a peptide comprising an amino acid sequence represented by SEQ ID NO: 1; a peptide comprising an amino acid sequence represented by SEQ ID NO: 2; a peptide comprising an amino acid sequence represented by SEQ ID NO: 3; a peptide comprising an amino acid sequence represented by SEQ ID NO: 4; a peptide comprising an amino acid sequence represented by SEQ ID NO: 5; a peptide comprising an amino acid sequence represented by SEQ ID NO: 12; a peptide comprising an amino acid sequence represented by SEQ ID NO: 14; and a peptide comprising an amino acid sequence represented by SEQ ID NO: 15.

In the present invention, the contents of SEQ ID NOs: 1 to 5, 12, 14 and 15 are as follows:

SEQ ID NO: 1:
Phe-$Xaa_1$-Ile-Gly-Arg-Leu ($FX_1IGRL$)

SEQ ID NO: 2:
$Xaa_2$-$Xaa_1$-Ile-Gly-Arg-Leu ($X_2X_1IGRL$)

SEQ ID NO: 3:
Phe-$Xaa_1$-$Xaa_3$-Gly-Arg-Leu ($FX_1X_3GRL$)

SEQ ID NO: 4:
Phe-$Xaa_1$-Ile-$Xaa_4$-Arg-Leu ($FX_1IX_4RL$)

SEQ ID NO: 5:
Phe-$Xaa_1$-Ile-Gly-$Xaa_5$-Leu ($FX_1IGX_5L$)

SEQ ID NO: 12:
Phe-$Xaa_1$-Ile-Gly-Arg-$Xaa_{12}$ ($FX_1IGRX_{12}$)

SEQ ID NO: 14:
$Xaa_1$-Phe-Cys-Ile-Gly-Arg-Leu ($X_1FCIGRL$)

SEQ ID NO: 15:
$Xaa_1$-Phe-Cys-Ile-Gly-Arg-$Xaa_{15}$ ($X_1FCIGRX_{15}$)

In above SEQ ID NO: 1, said $Xaa_1$ which is $X_1$, may be Dap($N_3$).

Said Dap($N_3$) means an amino acid sequence in which 3-azidoalanine forms a peptide bond with another amino acid.

A peptide having an amino acid sequence represented by above SEQ ID NO: 12 is a peptide in which a carboxyl group —COOH of leucine at the end of the peptide having the amino acid sequence represented by SEQ ID NO: 1 is transformed into —CONH$_2$ and has the same structure as shown in Formula 1 below. Thus, Xaa$_{12}$, which is X$_{12}$, means leucine in which the carboxyl group —COOH is transformed into —CONH$_2$. The peptide having an amino acid sequence represented by above SEQ ID NO: 12 has homology to the peptide having the amino acid sequence represented by SEQ ID NO: 1.

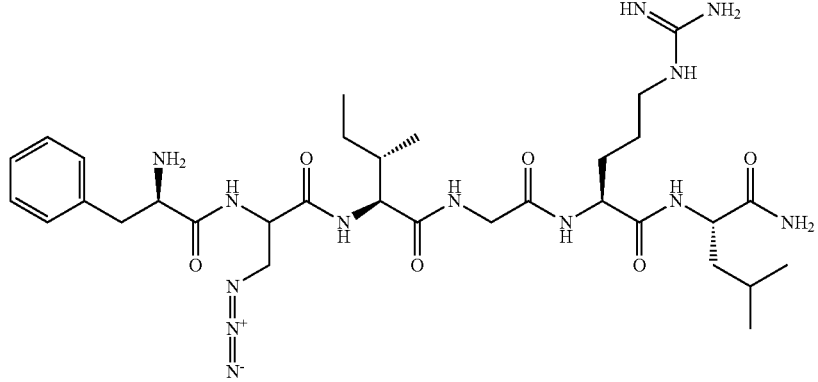

[Formula 1]

In above SEQ ID NO: 14, said Xaa$_1$, which is X$_1$, is Dap(N$_3$), which is as described above.

A peptide having an amino acid sequence represented by above SEQ ID NO: 15 is a peptide in which a carboxyl group —COOH of leucine at the end of the peptide having the amino acid sequence represented by SEQ ID NO: 14 is transformed into —CONH$_2$. Thus, Xaa$_{15}$, which is X$_{15}$, means leucine in which the carboxyl group —COOH is transformed into —CONH$_2$. The peptide having an amino acid sequence represented by above SEQ ID NO: 15 has homology to the peptide having the amino acid sequence represented by SEQ ID NO: 14.

In above SEQ ID NOs: 2 to 5, Xaa$_1$, which is X$_1$, is Dap(N$_3$), which is as described above. In above SEQ ID NO: 2, Xaa$_2$, which is X$_2$, may be any one selected from Ala, Val, Leu, Ile, Pro, Trp, Tyr and Met. In above SEQ ID NO: 3, Xaa$_3$, which is X$_3$, may be any one selected from Ala, Val, Leu, Pro, Trp and Met. In above SEQ ID NO: 4, Xaa$_4$, which is X$_4$, may be any one selected from Ser, Thr, Tyr, Asn, Ala and Gln. In above SEQ ID NO: 5, Xaa$_5$, which is X$_5$, may be any one selected from Lys and His.

In the present invention, an amino acid sequence having homology to the amino acid sequence of SEQ ID NO: 1 may mean a sequence in which one amino acid of above SEQ ID NO: 1 is substituted, and the amino acid sequence having homology to above SEQ ID NO: 1 may be any one of SEQ ID NOs: 2 to 5.

The peptide of the present invention may serve as a permeation enhancer capable of increasing the permeation and absorption of drugs administered together by opening a tight junction between mucosal (mucous membrane) cells. The peptide according to the present invention may be SEQ ID NO: 1 or have homology to above SEQ ID NO: 1, and may have the carboxyl group —COOH of leucine at the end of the amino acid sequence transformed into —CONH$_2$, or include an amino acid sequence comprising N$_3$, and thus the peptide may control a tight junction between mucosal cells so as to improve mucosal permeability, thereby serving as a permeation enhancer with an improved function of promoting the absorption of an active ingredient.

Thus, in case that the peptide of the present invention is administered together with an active ingredient such as a drug, etc., it is possible to promote the absorption of the active ingredient through a mucous membrane thereby improving the bioavailability of the active ingredient.

In particular, the peptide of the present invention may control the tight junction at a intercellular space between the cells, so that drugs can pass through a intercellular space route and thus drugs with low bioavailability can easily pass through the mucous membrane, especially that of small intestine, nasal cavity, oral cavity, skin, lungs, vagina, rectum, and colon, thereby easily improving the bioavailability of drugs with low bioavailability.

The peptide of the present invention may promote the absorption of fexofenadine, which is a paracellular marker for identifying the permeation of drugs through the intercellular space route, into the nasal mucous membrane. Fexofenadine is hardly absorbed into the mucous membrane in normal cell membranes with the tight junction, and thus is used as a marker for identifying the permeation of drugs through a intercellular space route. If the mucosal absorption of fexofenadine is increased by a permeation enhancer, in case that there is no cytotoxicity, it can be confirmed that the permeation enhancer opens a tight junction between the cells to promote the absorption of fexofenadine with excellent efficacy. However, said fexofenadine is one of the BCS Class III substances for identifying a drug permeation, and a paracellular marker is not limited to fexofenadine only. Drugs with low membrane permeability such as BCS Class III drugs (e.g., cimetidine, acyclovir, captopril, ranitidine, metformin, etc.) and IV drugs (e.g., cyclosporine A, ritonavir, saquinavir, taxol, biponazole, etc.) may be used, and protein drugs or peptide drugs (e.g., leuprorelin, exenatide, exedin, etc.) may be used. The substances that may be used as the paracellular marker correspond to active substances, and various examples are presented in the description of the active substances below.

It can be understood that the peptide or peptide multimer according to the present invention remarkably promotes the absorption of the active substances or drugs through the mucous membrane, and thus the peptide or peptide multimer of the present invention opens the tight junction between mucosal cells, thereby remarkably increasing the absorption of drugs through an intercellular space route (see Experimental Examples 1 to 3).

In the present invention, the amino acid sequence of the peptide has a direction from left to right, which is the conventional direction from an amino terminus to a carboxy terminus. In the amino acid sequence of the peptide, —NH$_2$, which is an amino group present at the end of amino acid, may be located at the left end, and —COOH, which is a carboxyl group present at the end of amino acid, may be located at the right end.

In the method of representing the amino acid sequence, the —NH$_2$ and —COOH markings at the left and right ends of the amino acid sequence may be omitted. Alternatively, in case that —NH$_2$ and —COOH are indicated at the left and right ends of the amino acid sequence, this may mean —NH$_2$ and —COOH at the ends of each amino acid included in the amino acid sequence. For example, above SEQ ID NO: 1 may represent FX$_1$IGRL(X$_1$=Dap(N$_3$)). In other words, Phe-Dap(N$_3$)—Ile-Gly-Arg-Leu may represent an unmodified amino acid sequence itself, which may be represented by NH$_2$—FX$_1$IGRL-COOH, H—FX$_1$IGRL-OH or FX$_1$IGRL. In the present invention, in case that —H at the left amino group end of the amino acid sequence or —OH at the right carboxyl group end thereof is substituted with X, it may be shown that NHX or X may be marked at the left end of the amino acid sequence, or COX or X may be marked at the right end thereof. For example, in case that OH of —COOH of leucine at the right of SEQ ID NO: 1 is substituted with NH$_2$, this case may be represented by FX$_1$IGRL-CONH$_2$ or FX$_1$IGRL-NH$_2$.

In the present invention, the "mucous membrane" may refer to a soft tissue that forms the inner wall of the respiratory tract, digestive tract, and reproductive tract coming into direct contact with the outside, and may be involved in functions related to absorption and secretion of substances. In the present invention, the type of the mucous membrane is not particularly limited, but may be a mucous membrane in which the tight junction is expressed. Preferably, the mucous membrane may be the mucous membrane of oral cavity, nasal cavity, small intestine, large intestine, rectum, vagina, lungs, skin, etc., more preferably small intestine mucous membrane or nasal cavity mucous membrane.

The present invention provides a composition for promoting mucous membrane permeation including a peptide multimer in which at least two peptides are linked, wherein each of the at least two peptides is selected from the group consisting of: a peptide comprising an amino acid sequence represented by SEQ ID NO: 1; a peptide comprising an amino acid sequence represented by SEQ ID NO: 6; a peptide comprising an amino acid sequence represented by SEQ ID NO: 12; a peptide comprising an amino acid sequence represented by SEQ ID NO: 13; a peptide comprising an amino acid sequence represented by SEQ ID NO: 14; and a peptide comprising an amino acid sequence represented by SEQ ID NO: 15.

The description of SEQ ID NOs: 1, 12, 14, 15, mucous membrane and the like are as described above.

SEQ ID NO: 6 of the present invention may have H—FCIGRL-OH, that is, an amino acid sequence of Phe-Cys-Ile-Gly-Arg-Leu.

A peptide having an amino acid sequence represented by SEQ ID NO: 13 of the present invention is a peptide which has Phe-Cys-Ile-Gly-Arg-$Xaa_{13}$ ($FCIGRX_{13}$), that is, H—FCIGRL-$NH_2$ and in which a carboxyl group —COOH of leucine at the end of the peptide having the amino acid sequence represented by SEQ ID NO: 6 is transformed into —$CONH_2$. Thus, $Xaa_{13}$, which is $X_{13}$, means leucine in which the carboxyl group —COOH is transformed into —$CONH_2$. A peptide having an amino acid sequence represented by above SEQ ID NO: 13 has homology to the peptide having the amino acid sequence represented by SEQ ID NO: 6. For a detailed description of the amino acid sequence of the peptide and the method of representing the amino acid sequence, see the description of the peptide having the amino acid sequence represented by SEQ ID NO: 1.

In the present invention, the peptide multimer may mean that at least two peptides are linked, in which the two or more peptides are the same or different from each other.

In the present invention, a linkage method of the peptides constituting a multimer may be a disulfide bond in which S of cystein is bonded to each other, but is not limited thereto.

According to the present invention, specific methods for linking and synthesizing a dimer and a multimer may be found from Korean Patent Publication No. 10-2014-0056396; Design, Synthesis, and Functionalization of Dimeric Peptides Targeting Chemokine Receptor CXCR4 (dx.doi.org/10.1021/jm2009716|J. Med. Chem. 2011, 54, 7648-7662) and Synthesis and Activity Profiles of Novel Cyclic Opioid Peptide Monomers and Dimers J. Med. Chem. 1985, 28, 1766-1771.

The peptide multimer may be a peptide dimer, and each of the peptides constituting the peptide dimer may be the same or different from each other, and the linkage method thereof is not limited. Specifically, the peptide dimer may be: 1) a peptide dimer in which H—FCIGRL-$NH_2$ (SEQ ID NO: 13) and H—FCIGRL-OH (SEQ ID NO: 6) are linked; 2) a peptide dimer in which H—FCIGRL-$NH_2$ (SEQ ID NO: 13) and H—FCIGRL-$NH_2$ (SEQ ID NO: 13) are linked; 3) a peptide dimer in which H—FCIGRL-OH (SEQ ID NO: 6) and H—FCIGRL-OH (SEQ ID NO: 6) are linked; 4) a peptide dimer in which H—$FX_1$IGRL-$NH_2$ (SEQ ID NO: 12) and H—FCIGRL-$NH_2$ (SEQ ID NO: 13) are linked; 5) a peptide dimer in which H—$FX_1$IGRL-OH (SEQ ID NO: 1) and H—FCIGRL-OH (SEQ ID NO: 6) are linked; 6) a peptide dimer in which H—$FX_1$IGRL-$NH_2$ (SEQ ID NO: 12) and H—FCIGRL-OH (SEQ ID NO: 6) are linked; 7) a peptide dimer in which H—$FX_1$IGRL-OH (SEQ ID NO: 1) and H—FCIGRL-$NH_2$ (SEQ ID NO: 13) are linked; 8) a peptide dimer in which H—$FX_1$IGRL-$NH_2$ (SEQ ID NO: 12) and H—FX1IGRL-$NH_2$ (SEQ ID NO: 12) are linked; 9) a peptide dimer in which H—$FX_1$IGRL-$NH_2$ (SEQ ID NO: 12) and H—$FX_1$IGRL-OH (SEQ ID NO: 1) are linked; or 10) a peptide dimer in which H—$FX_1$IGRL-OH (SEQ ID NO: 1) and H—$FX_1$IGRL-OH (SEQ ID NO: 1) are linked; 11) a peptide dimer in which $X_1$FCIGRL-OH (SEQ ID NO: 14) and H—$FX_1$IGRL-OH (SEQ ID NO: 1) are linked; 12) a peptide dimer in which $X_1$FCIGRL-OH (SEQ ID NO: 14) and H—FCIGRL-OH (SEQ ID NO: 6) are linked; 13) a peptide dimer in which $X_1$FCIGRL-OH (SEQ ID NO: 14) and H—$FX_1$IGRL-$NH_2$ (SEQ ID NO: 12) are linked; 14) a peptide dimer in which $X_1$FCIGRL-OH (SEQ ID NO: 14) and H—FCIGRL-$NH_2$(SEQ ID NO: 13) are linked; 15) a peptide dimer in which $X_1$FCIGRL-OH (SEQ ID NO: 14) and $X_1$FCIGRL-OH (SEQ ID NO: 14) are linked; 16) a peptide dimer in which X₁FCIGRL-OH (SEQ ID NO: 14) and X₁FCIGRL-NH₂ (SEQ ID NO: 15) are linked; 17) a peptide dimer in which X₁FCIGRL-NH₂ (SEQ ID NO: 15) and H—FX₁IGRL-OH (SEQ ID NO: 1) are linked; 18) a peptide dimer in which X₁FCIGRL-NH₂ (SEQ ID NO: 15) and H—FCIGRL-OH (SEQ ID NO: 6) are linked; 19) a peptide dimer in which X₁FCIGRL-NH₂ (SEQ ID NO: 15) and H—FX₁IGRL-NH₂ (SEQ ID NO: 12) are linked; 20) a peptide dimer in which X₁FCIGRL-NH₂ (SEQ ID NO: 15) and H—FCIGRL-NH₂ (SEQ ID NO: 13) are linked; and 21) a peptide dimer in which X₁FCIGRL-NH₂ (SEQ ID NO: 15) and X₁FCIGRL-NH₂ (SEQ ID NO: 15) are linked, but is not limited thereto.

As one example of the peptide multimer linkage method of the present invention, the peptide comprising the H—FCIGRL-NH₂ amino acid sequence of SEQ ID NO: 13 may be linked by a disulfide bond, and the peptide dimer in which two peptides are bonded may be represented as shown in Formula 2 below, wherein each of the two peptides is represented by SEQ ID NO: 13.

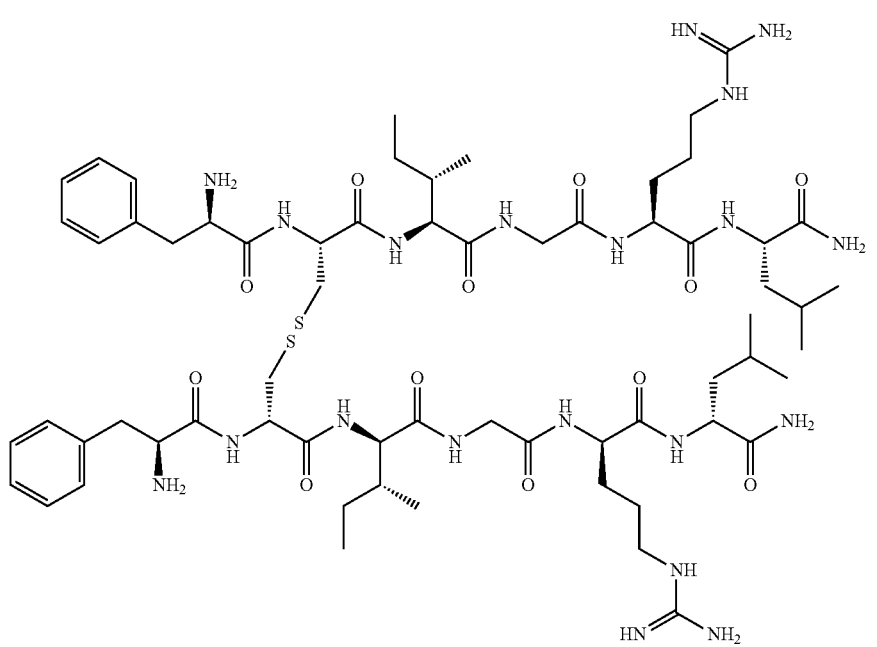

[Formula 2]

In addition, a peptide comprising the amino acid sequence of X₁FCIGRL-NH₂, which is above SEQ ID NO: 15 may also be linked by a disulfide bond, and a peptide dimer in which two peptides are bonded may be represented as shown in Formula 3 below, wherein each of the two peptides is represented by above SEQ ID NO: 13.

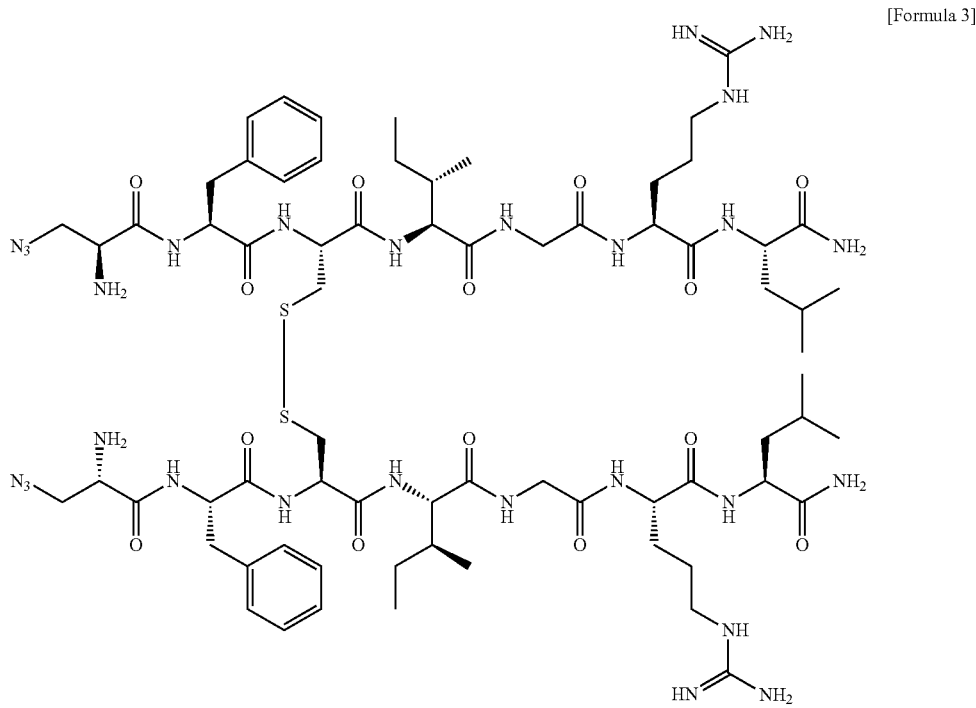 [SMILES: CC[C@H](C)[C@H](NC(=O)[C@H](CSSC[C@H](NC(=O)[C@H](Cc1ccccc1)NC(=O)[C@@H](N)CN=[N+]=[N-])C(=O)N[C@H](C(=O)NCC(=O)N[C@@H](CCCNC(=N)N)C(=O)N[C@@H](CC(C)C)C(N)=O)[C@@H](C)CC)NC(=O)[C@H](Cc1ccccc1)NC(=O)[C@@H](N)CN=[N+]=[N-])C(=O)NCC(=O)N[C@@H](CCCNC(=N)N)C(=O)N[C@@H](CC(C)C)C(N)=O]

[Formula 3]

The peptide multimer may play the same role as a peptide having an amino acid represented by SEQ ID NO: 1. In other words, the peptide multimer may serve as a permeation enhancer capable of increasing the permeation and absorption of drugs administered together by opening a tight junction between mucosal cells. For the specific description thereof, it is possible to see the above description of the peptide having the amino acid sequence represented by SEQ ID NO: 1.

According to one example of the present invention, the peptide multimer may be a peptide dimer in which two peptides are linked, wherein each of the two peptides comprises an amino acid sequence represented by SEQ ID NO: 6; a peptide dimer in which two peptides are linked, wherein each of the two peptides comprises an amino acid sequence represented by SEQ ID NO: 13; a peptide dimer in which two peptides are linked, wherein each of the two peptides comprises an amino acid sequence represented by SEQ ID NO: 15; or a mixture thereof.

The present invention provides a composition for promoting mucous membrane permeation including a peptide multimer in which at least two peptides are linked, wherein each of the at least two peptides is selected from the group consisting of: a peptide comprising an amino acid sequence represented by SEQ ID NO: 2; a peptide comprising an amino acid sequence represented by SEQ ID NO: 3; a peptide comprising an amino acid sequence represented by SEQ ID NO: 4; a peptide comprising an amino acid sequence represented by SEQ ID NO: 5; a peptide comprising an amino acid sequence represented by SEQ ID NO: 7; a peptide comprising an amino acid sequence represented by SEQ ID NO: 8; a peptide comprising an amino acid sequence represented by SEQ ID NO: 9; a peptide comprising an amino acid sequence represented by SEQ ID NO: 10; and a peptide comprising an amino acid sequence represented by SEQ ID NO: 11.

The description of SEQ ID NOs: 2 to 5, mucous membrane, peptide multimer, etc., are as described above.

In the present invention, an amino acid sequence having homology to the amino acid sequence of SEQ ID NO: 6 may mean a sequence in which one amino acid of above SEQ ID NO: 6 is substituted, and the amino acid sequence having homology to above SEQ ID NO: 6 may be any one of SEQ ID NOs: 7 to 11 below.

```
SEQ ID NO: 7:
Xaa7-Cys-Ile-Gly-Arg-Leu (X7CIGRL)

SEQ ID NO: 8:
Phe-Xaa8-Ile-Gly-Arg-Leu (FX8IGRL)

SEQ ID NO: 9:
Phe-Cys-Xaa9-Gly-Arg-Leu (FCX9GRL)

SEQ ID NO: 10:
Phe-Cys-Ile-Xaa10-Arg-Leu (FCIX10RL)

SEQ ID NO: 11:
Phe-Cys-Ile-Gly-Xaa11-Leu (FCIGX11L)
```

In above SEQ ID NO: 7, $Xaa_7$, which is $X_7$, may be Ala, Val, Leu, Ile, Pro, Trp, Tyr or Met. In above SEQ ID NO: 8, $Xaa_8$, which is $X_8$, may be Gly, Ser, Thr, Tyr, Asn or Gln. In SEQ ID NO: 9, $Xaa_9$, which is $X_9$, may be Ala, Val, Leu, Pro, Trp or Met. In above SEQ ID NO: 10, $Xaa_{10}$, which is $X_{10}$, may be Ser, Thr, Tyr, Asn, Ala or Gln. In above SEQ ID NO: 11, $Xaa_{11}$, which is $X_{11}$, may be Lys or His.

The peptide multimer may play the same role as the peptide having an amino acid represented by SEQ ID NO: 1. In other words, the peptide multimer may serve as a permeation enhancer capable of increasing the permeation and absorption of drugs administered together by opening a tight junction between mucosal cells. For the specific description thereof, it is possible to see the above description of the peptide having the amino acid sequence represented by SEQ ID NO: 1.

In one example of the present invention, said composition may further include an active ingredient.

In case that the peptide or peptide multimer of the present invention is administered together with an active ingredient, the peptide or peptide multimer can control a tight junction present in the mucous membrane, so that the active ingredient can easily pass through the mucous membrane, so as to promote absorption of the active ingredient. For example, in the case that the peptide is orally (enterally) administered together with an active ingredient, the peptide can open a tight junction present in the mucous membrane of small intestine, so that the active ingredient can pass through the mucous membrane, thereby promoting absorption of the active ingredient and remarkably improving the bioavailability of the active ingredient. Thus, in case that the active ingredient with low bioavailability are administered together with the peptide or peptide multimer, the drug efficacy of the active ingredient can be remarkably improved.

In the present invention, the type of the active ingredient is not particularly limited, but may be an active ingredient that penetrates the mucous membrane (biomembrane) made of a tight junction between cells by passive transport, and it may be a substance that needs to improve the bioavailability of the active ingredient. The active ingredient may be an anticancer agent, an antibiotic agent, an anti-inflammatory agent, an analgesic agent, an immunosuppressive agent (immunosuppressants), a peptide, a hormone, a substance derived from a natural product, or a mixture thereof. For example, the active ingredient may include insulin, leuprorelin, exenatide, fexofenadine, paclitaxel, acyclovir, cyclosporin A, FK506, prednisone, methylprednisolone, cyclophosphamide, thalidomide, azathioprine and daclizumab, physalin B, physalin F, physalin G, seco-steroids purified from *Physalis angulata* L, 15-deoxyspergualin (DSG, 15-dos), MMF, rapamycin and derivatives thereof, CCI-779, FR 900520, FR 900523, NK86 1086, depsidomycin, kanglemycin-C, spergualin, prodigiosin 25-c, cammunomicin, demethomycin, tetranactin, tranilast, stevastelins, myriocin, gliooxin, FR 651814, SDZ214104, bredinin, WS9482, mycophenolic acid, mimoribine, misoprostol, OKT3, Anti-IL-2 receptor antibodies, azasporine, leflunomide, mizoribine, azaspirane (SKF 105685), paclitaxel, altretamine, busulfan, chlorambucil, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, atenolol, propranolol, doxorubicin, ritonavir, saquinavir, rutin, hydroxyurea, and derivatives or mixtures thereof.

Preferably, the active ingredient may be insulin, paclitaxel, acyclovir, cyclosporin A, fexofenadine, doxirubicin, ritonavir, saquinavir, atenolol, rutin, exenatide, or mixtures thereof.

In addition, the active ingredient may be a drug belonging to Class III or Class IV of the Biopharmaceutics Classification System (BCS).

In addition, the active ingredient may be selected from the group consisting of chemotherapeutic agents, gene therapy vectors, growth factors, contrast agents, angiogenesis factors, radioactive nuclides, anti-infective agents, anti-tumor compounds, and receptor-binding agents. Particularly, the active ingredient may include plasma lysate, platelet inhibitors, calcium channel blockers, nitrate, phosphate inhibitors, plasma inhibitors, plasma inhibitors, plasma inhibitors, platelet reducing agents, antithrombotic agents, antibacterial agents, antibiotics, glycoprotein IIb/IIIa inhibitors, inhibitors of cell surface glycoprotein receptors, antiplatelet agents, antithrombotic agents, microtubule inhibitors, retinoids, antifungal agents, anti-oxypeptides, actin inhibitors, modification inhibitors, antisense nucleotide, molecular genetic intervention agents, anti-metabolic agents, antiproliferative agents, anticancer agents, dexametha nonsteroidal anti-inflammatory agents, immunosuppressants, PDGF antagonists, growth hormone antagonists, growth factor antibodies, anti-growth factor antibodies, growth factor antagonists, radiotherapy agents, iodine-containing compounds, barium-containing compounds, heavy metals acting as radiopaque agents, peptides, proteins, enzymes, extracellular matrix components, cellular components, angiotensin converting enzyme anti-inflammatory agents, antibacterial agents, and combinations thereof. In addition, the active ingredient may include parathyroid hormone, heparin, human growth hormone, covalent heparin, hirudin, hirulog, argatroban, D-phenylalanyl-L-poly-L-arginyl chloromethyl ketone, urokinase, streptokinase, nitric oxide, triclopidine, aspirin, colchicine, dimethyl sulfoxide, cytochalasin, deoxyribonucleic acid, methotrexate, tamoxifen citrate, dexamethasone, dexamethasone sodium phosphate, dexamethasone acetate, cyclosporin, trapidal, angiopeptin, angiogenin, dopamine, 'Co, "Ir, P. '"In, 'Y.99mTc, pergolide mesylate, bromocriptine mesylate, gold, tantalum, platinum, tungsten, captopril, enalapril, ascorbic acid, C-tocopherol, superoxide dismutase, deferoxamine, estrogen, azidothymidine (AZT), acyclovir, famciclovir, rimantadine hydrochloride, ganciclovir sodium, 5-aminolevulinic acid, meta-tetrahydroxyphenylchlorin, hexadecafluoro zinc phthalocyanine, tetramethyl hematoporphyrin and rhodamine 123, and combinations thereof.

In the present invention, the content of the peptide or peptide multimer in the composition is not particularly limited unless the effect thereof is limited, but the composition may include 0.001 to 50 wt % of the peptide or peptide multimer.

In the present invention, an administration route and frequency of the composition may be appropriately adjusted according to the type of active ingredient included, a patient's condition, and a degree of disease.

In the present invention, the composition may be administered on various routes, and may be administered enterally, nasally, oromucosally, transdermally, transpulmonarily, rectally or vaginally.

In the present invention, the composition may be administered once a day or multiple times a day.

In the present invention, the composition may further include a protease inhibitor, that is, a proteolytic enzyme inhibitor. The type of the protease inhibitor is not particularly limited unless the effect of the composition is suppressed. For example, the composition may include bestatin, L-trans-3-carboxyoxiran-2-carbonyl-L-leucylagmatine, ethylenediaminetetra acetic acid (EDTA), phenylmethylsulfonylfluoride (PMSF), aprotinin, amyloid protein precursor (APP), amyloid beta precursor protein, C-proteinase inhibitor, collagen VI, bovine pancreatic trypsin inhibitor (BPTI), 4-(2-aminoethyl)-benzenesulfonylfluoride (AEBSF), antipain, benzamidine, chymostatin, e-aminocaproate, N-ethylmaleimide, leupeptin, pepstatin A, phosphoramidon or combinations thereof.

In the present invention, the composition may include pharmaceutically acceptable adjuvants or additives. The adjuvants or additives to be used may include saline solution, sterilized water, Ringer's solution, buffered saline, dextrose solution, maltodextrin solution, glycerol, ethanol, amino acid and a combination of at least one component thereof, and other conventional additives such as stabilizers, mucoadhesives, antioxidants, buffer solutions, bacteriostatic agents, etc., may be added, if needed. Also, the composition may be formulated into liquid medicines such as aqueous solutions, suspensions, emulsions, etc., pills, capsules, granules or tablets with the addition of diluents, dispersing agents, surfactants, binders and lubricants.

The present invention provides a formulation including at least one peptide selected from the group consisting of: a peptide comprising an amino acid sequence represented by SEQ ID NO: 1; a peptide comprising an amino acid sequence represented by SEQ ID NO: 2; a peptide comprising an amino acid sequence represented by SEQ ID NO: 3; a peptide comprising an amino acid sequence represented by SEQ ID NO: 4; a peptide comprising an amino acid sequence represented by SEQ ID NO: 5; a peptide comprising an amino acid sequence represented by SEQ ID NO: 12; a peptide comprising an amino acid sequence represented by SEQ ID NO: 14; and a peptide comprising an amino acid sequence represented by SEQ ID NO: 15, and an active ingredient.

In addition, the present invention provides a formulation including a peptide multimer in which at least two peptides are linked, wherein each of the at least two peptides is selected from the group consisting of: a peptide comprising an amino acid sequence represented by SEQ ID NO: 1; a peptide comprising an amino acid sequence represented by SEQ ID NO: 6; a peptide comprising an amino acid sequence represented by SEQ ID NO: 12; a peptide having an amino acid sequence represented by SEQ ID NO: 13; a peptide comprising an amino acid sequence represented by SEQ ID NO: 14; and a peptide comprising an amino acid sequence represented by SEQ ID NO: 15, and an active ingredient.

The formulation of the present invention may include the peptide or the peptide multimer, so as to remarkably improve the bioavailability of the active ingredient. As described above, the peptide or the peptide multimer may control the tight junction present in the mucous membrane so as to promote absorption of the active ingredient, thereby maximizing the therapeutic effect of the active ingredient.

According to one example of the present invention, the peptide multimer may be a peptide dimer in which two peptides are linked, wherein each of the two peptides comprises an amino acid sequence represented by SEQ ID NO: 6; a peptide dimer in which two peptides are linked, wherein each of the two peptides comprises an amino acid sequence represented by SEQ ID NO: 13; a peptide dimer in which two peptides are linked, wherein each of the two peptides comprises an amino acid sequence represented by SEQ ID NO: 15; or a mixture thereof.

The present invention provides a formulation including a peptide multimer in which at least two peptides are linked, wherein each of the at least two peptides is selected from the group consisting of: a peptide comprising an amino acid sequence represented by SEQ ID NO: 2; a peptide comprising an amino acid sequence represented by SEQ ID NO: 3; a peptide comprising an amino acid sequence represented by SEQ ID NO: 4; a peptide comprising an amino acid sequence represented by SEQ ID NO: 5; a peptide comprising an amino acid sequence represented by SEQ ID NO: 7; a peptide comprising an amino acid sequence represented by SEQ ID NO: 8; a peptide comprising an amino acid sequence represented by SEQ ID NO: 9; a peptide comprising an amino acid sequence represented by SEQ ID NO: 10; and a peptide comprising an amino acid sequence represented by SEQ ID NO: 11, and an active ingredient.

The description of SEQ ID NOs: 2 to 5, 7 to 11 and the like are as described above.

The formulation according to the present invention may further include a pharmaceutically acceptable adjuvant or additive in addition to the peptide and the active ingredient. The kind of the pharmaceutically acceptable adjuvant or additive is not limited unless it interferes with the effect of the peptide and the active ingredient, and known pharmaceutically acceptable additives may be used.

In the present invention, the pharmaceutically acceptable adjuvant or additive may be appropriately selected according to the route of administration of the formulation. For example, if the formulation is orally (enterally) administered, it may be possible to use a pharmaceutically acceptable additive for preventing degradation of the peptide in the stomach.

In the present invention, the pharmaceutically acceptable adjuvants or additives to be used may include saline solution, sterilized water, Ringer's solution, buffered saline, dextrose solution, maltodextrin solution, glycerol, ethanol, amino acid and a combination of at least one component thereof, and other conventional additives such as stabilizers, mucoadhesives, antioxidants, buffer solutions, bacteriostatic agents, etc., may be added, if needed. Also, the formulation may be formulated into liquid medicines such as aqueous solutions, suspensions, emulsions, etc., pills, capsules, granules or tablets with the addition of diluents, dispersing agents, surfactants, binders and lubricants. Thus, the composition of the present invention may be patches, liquid medicines, pills, capsules, granules, tablets, suppositories, etc. Such formulation may be prepared according to a conventional method used for formulation in the art or a method disclosed in Remington's Pharmaceutical Science (18th edition), Merck Publishing Company, Easton PA, and such formulation may be formulated into various formulations depending on each disease or component.

The formulation of the present invention may be a formulation is formulated for administering enterally, nasally, oromucosally, transdermally, transpulmonarily, rectally, and vaginally, and may be appropriately formulated into a dosage form for this purpose.

The peptide or the peptide multimer of the present invention may be orally (enterally) or parenterally administered (for example, applied intravenously, hypodermically, intraperitoneally or locally) according to a targeted method, in which a dosage varies in a range thereof depending on a patient's weight, age, gender, health condition and diet, an administration time, an administration method, an excretion rate, a severity of a disease and the like.

In the present invention, the type of the active ingredient included in the formulation is not particularly limited, and may preferably be a material requiring improved bioavailability, and the type is as mentioned above.

The present invention provides a cosmetic composition including at least one peptide selected from the group consisting of: a peptide comprising an amino acid sequence represented by SEQ ID NO: 1; a peptide comprising an amino acid sequence represented by SEQ ID NO: 2; a peptide comprising an amino acid sequence represented by SEQ ID NO: 3; a peptide comprising an amino acid sequence represented by SEQ ID NO: 4; a peptide comprising an amino acid sequence represented by SEQ ID NO: 5; a peptide comprising an amino acid sequence represented by SEQ ID NO: 12; a peptide comprising an amino acid sequence represented by SEQ ID NO: 14; and a peptide comprising an amino acid sequence represented by SEQ ID NO: 15.

The description of SEQ ID NO, etc., are as described above.

The present invention provides a cosmetic composition including a peptide multimer in which at least two peptides are linked, wherein each of the at least two peptides is selected from the group consisting of: a peptide comprising an amino acid sequence represented by SEQ ID NO: 1; a peptide comprising an amino acid sequence represented by SEQ ID NO: 6; a peptide comprising an amino acid sequence represented by SEQ ID NO: 12; and a peptide comprising an amino acid sequence represented by SEQ ID NO: 13; a peptide comprising an amino acid sequence represented by SEQ ID NO: 14; and a peptide comprising an amino acid sequence represented by SEQ ID NO: 15.

The description of SEQ ID NO, multimer, etc., are as described above.

According to one example of the present invention, the peptide multimer may be a peptide dimer in which two peptides are linked, wherein each of the two peptides comprises an amino acid sequence represented by SEQ ID NO: 6; a peptide dimer in which two peptides are linked, wherein the peptide comprises an amino acid sequence represented by SEQ ID NO: 13; a peptide dimer in which two peptides are linked, wherein the peptide comprises an amino acid sequence represented by SEQ ID NO: 15; or a mixture thereof.

In one example of the present invention, said composition may further include an active ingredient.

The present invention provides a cosmetic composition including a peptide multimer in which at least two peptides are linked, wherein each of the at least two peptides is selected from the group consisting of: a peptide comprising an amino acid sequence represented by SEQ ID NO: 2; a peptide comprising an amino acid sequence represented by SEQ ID NO: 3; a peptide comprising an amino acid sequence represented by SEQ ID NO: 4; a peptide comprising an amino acid sequence represented by SEQ ID NO: 5; a peptide comprising an amino acid sequence represented by SEQ ID NO: 7; a peptide comprising an amino acid sequence represented by SEQ ID NO: 8; a peptide comprising an amino acid sequence represented by SEQ ID NO: 9; a peptide comprising an amino acid sequence represented by SEQ ID NO: 10; and a peptide comprising an amino acid sequence represented by SEQ ID NO: 11.

The description of SEQ ID NO, multimer, etc., are as described above.

In the cosmetic composition of the present invention, the peptide or the peptide multimer may be added to the cosmetic in an amount of 0.001 to 10.0 wt % based on the total weight of the cosmetic composition.

Ingredients contained in the cosmetic composition of the present invention may include ingredients commonly used in cosmetic compositions in addition to the peptide or the peptide multimer as an effective ingredient, and may include conventional adjuvants such as antioxidants, stabilizers, solubilizers, vitamins, pigments, pigments, and fragrances, and carriers.

The cosmetic composition of the present invention may be prepared in any formulation conventionally prepared in the art, for example, solution, suspension, emulsion, paste, gel, cream, lotion, powder, soap, surfactant-containing cleansing, oil, powder foundation, emulsion foundation, wax foundation, spray and the like, but is not limited thereto. More particularly, the cosmetic composition may be prepared in the form of skin lotion, nutritional lotion, nutritional cream, massage cream, essence, pack, eye cream, cleansing cream, cleansing foam, cleansing water, pack, spray, or powder.

In addition, the present invention provides a use of the peptide or the peptide multimer for promoting mucous membrane permeation of an active ingredient.

The present invention provides a use of the peptide or the peptide multimer in the manufacture of a medicament for promoting mucous membrane permeation of an active ingredient.

The present invention provides a method for promoting mucous membrane permeation of an active ingredient, comprising a step of administering the peptide or the peptide multimer into a subject.

As used herein, the "subject" means mammals including humans, and the "administration" means providing a predetermined material to a patient by means of any appropriate method.

In the case that peptide or peptide multimer of the present invention is administered together with an active ingredient, the peptide or peptide multimer can control a tight junction present in the mucous membrane, so that the active ingredient can easily pass through the mucous membrane, so as to promote absorption of the active ingredient. For example, in the case that the peptide or the peptide multimer of the present invention is orally (enterally) administered together with an active ingredient, the peptide or the peptide multimer can open a tight junction present in the mucous membrane of small intestine, so that the active ingredient can pass through the mucous membrane of small intestine, so as to promote absorption of the active ingredient, thereby remarkably improving the bioavailability of the active ingredients. Thus, if active ingredient with low bioavailability are administered together with the peptide or the peptide multimer, medical efficacy of the active ingredient may be remarkably improved.

Matters mentioned in the composition, use, method and formulation of the present invention are applied the same, if not contradictory to each other.

Advantageous Effects

A peptide or a peptide multimer according to the present invention serves to control a tight junction between cells, so as to improve mucosal permeability, thereby facilitating the absorption, through a mucous membrane, of an active ingredient of co-administered drugs and the like. Thus, the bioavailability of the active ingredient can be significantly improved, and as a result, the therapeutic effect of the active ingredient can be significantly improved.

MODE FOR INVENTION

Figure 1:
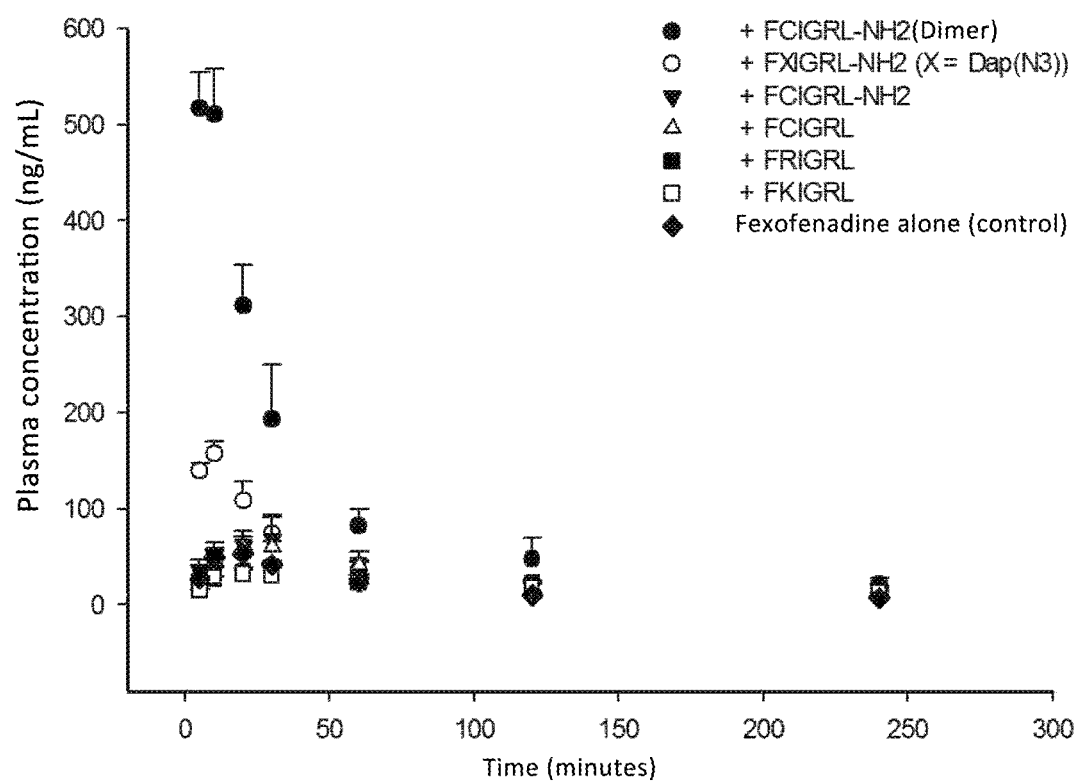
FIG. 1 is a time-concentration graph for confirming the degree of absorption of fexofenadine in the nasal mucous membrane with regard to the composition including peptides prepared according to Examples 1 and 2 and Comparative Examples 1 to 4 of the present invention, respectively.

Hereinafter, the present invention will be described in detail through Examples for better understanding of the present invention. However, the following Examples are provided only for the purpose of illustrating the present invention, and thus the scope of the present invention is not limited thereto. The Examples of the present invention are provided to more completely describe the present invention to those having ordinary skill in the art, to which the present invention pertains.

Meanwhile, with regard to the materials used in the present invention, the reagents used for preparing peptides were purchased from AnaSpec (Fremont, CA, USA), and the reagents used for preparing the composition and the formulation were purchased from Sigma-Aldrich (St. Louis, MO, USA) unless otherwise specified.

<Preparation Example 1> Synthesis of FCIGRL-NH$_2$

The above modified peptide was prepared in such a way that —OH of the carboxyl group —COOH at the end of L of FCIGRL is substituted with —NH$_2$. In the preparation method, ① NH$_2$-Leu-MBHA link amide resin, in which leucine is attached to resin, was used.

② All amino acid raw materials used for peptide synthesis have the amino group end protected by Fmoc, and those (Fmoc-Phe-OH, Fmoc-Cys(Trt)-OH, Fmoc-Ile-OH, Fmoc-Gly-OH, Fmoc-Arg(Pbf)-OH, etc.) protected by Trt, Boc, t-Bu, etc., which are all removed from acid (TFA, Trifluoroacetic acid), were used for residues.

③ For coupling, the protected amino acids and a coupling reagent HBTU/HOBt/NMM were dissolved in DMF, added to the prepared NH$_2$-Leu-MBHA link amide resin, and then reacted for two hours. After the reaction, the resin was washed in the order of DMF, MeOH, and DMF.

④ To remove Fmoc, 20% piperidine dissolved in DMF was added and reacted twice for 5 minutes at room temperature. After the reaction, the resin was washed in the order of DMF, MeOH, and DMF.

⑤ By repeating the above steps, cleavage cocktail (TFA/EDT/Thioanisole/TIS/H$_2$O=90/2.5/2.5/2.5/2.5) was added to the peptide base skeleton (NH$_2$-Phe-Cys-Ile-Gly-Arg-Leu-MBHA link amide resin) so as to remove the protecting group of the peptide residue and separate the peptide from the resin.

⑥ After adding cooling diethyl ether 10 times the amount of the separated peptide in step ⑤ to precipitate the peptide, the resulting solution was centrifuged at 3000 rpm for 10 minutes to discard the clarified liquid, and then cooling diethyl ether was further added twice and centrifuged to obtain the peptide, and then the resulting peptide was purified with Prep-HPLC and freeze-dried.

<Preparation Example 2> Preparation of FCIGRL

FCIGRL was synthesized and prepared by coupling one by one from the end of the carboxyl group using the Fmoc solid phase peptide synthesis (SPPS) method. In other words, ① NH$_2$-Leu-2-chloro-trityl resin, in which leucine is attached to resin, was used.

② All amino acid raw materials used for peptide synthesis have the amino group end protected by Fmoc, and those (Fmoc-Phe-OH, Fmoc-Cys(Trt)-OH, Fmoc-Ile-OH, Fmoc-Gly-OH, Fmoc-Arg(Pbf)-OH, etc.) protected by Trt, Boc, t-Bu, etc., which are all removed from acid (TFA, Trifluoroacetic acid), were used for residues.

③ For coupling, the protected amino acids and a coupling reagent HBTU/HOBt/NMM ((HBTU=2-(1H-benzotriazole-1-yl)-1,1,3,3-tetramethylaminium hexafluorophosphate; HOBt=N-Hydroxxybenzotriazole; NMM=4-Methylmorpholine) were dissolved in DMF, added to the prepared NH$_2$-leu-2-chloro-trityl resin, and reacted for two hours. After the reaction, the resin was washed in the order of DMF, MeOH, and DMF.

④ To remove Fmoc, 20% piperidine dissolved in DMF was added and reacted twice for 5 minutes at room temperature. After the reaction, the resin was washed in the order of DMF, MeOH, and DMF.

⑤ By repeating each of the above steps, the peptide base skeleton (NH$_2$-Phe-Cys-Ile-Gly-Arg-Leu-2-chloro-trityl resin) was made, after which cleavage cocktail (TFA/EDT/Thioanisole/TIS/H$_2$O=90/2.5/2.5/2.5/2.5) ((TFA=trifluoroacetic acid; EDT=1,2-ethanedithiol; TIS=triisopropylsilane) was added to remove the protecting group of the peptide residue and separate the peptide from the resin.

⑥ After adding cooling diethyl ether 10 times the amount of the separated peptide in step ⑤ to precipitate the peptide, the resulting solution was centrifuged at 3000 rpm for 10 minutes to discard the clarified liquid, and then cooling diethyl ether was further added twice and centrifuged to obtain the peptide, and then the resulting peptide was purified with Prep-HPLC and freeze-dried.

<Preparation Example 3> Preparation of FRIGRL

FRIGRL was synthesized and prepared by coupling one by one from the end of the carboxyl group using the Fmoc solid phase peptide synthesis (SPPS) method. In other words, ① NH$_2$-Leu-2-chloro-trityl resin, in which leucine is attached to resin, was used.

② All amino acid raw materials used for peptide synthesis have the amino group end protected by Fmoc, and those (Fmoc-Phe-OH, Fmoc-Ile-OH, Fmoc-Gly-OH, Fmoc-Arg(Pbf)-OH, etc.) protected by Trt, Boc, t-Bu, etc., which are all removed from acid (TFA, Trifluoroacetic acid), were used for residues.

③ For coupling, the protected amino acids and a coupling reagent HBTU/HOBt/NMM ((HBTU=2-(1H-benzotriazole-1-yl)-1,1,3,3-tetramethylaminium hexafluorophosphate; HOBt=N-Hydroxxybenzotriazole; NMM=4-Methylmorpholine) were dissolved in DMF, added to the prepared NH$_2$-leu-2-chloro-trityl resin, and reacted for two hours. After the reaction, the resin was washed in the order of DMF, MeOH, and DMF.

④ To remove Fmoc, 20% piperidine dissolved in DMF was added and reacted twice for 5 minutes at room temperature. After the reaction, the resin was washed in the order of DMF, MeOH, and DMF.

⑤ By repeating each of the above steps, the peptide base skeleton (NH$_2$-Phe-Arg-Ile-Gly-Arg-Leu-2-chloro-trityl resin) was made, after which cleavage cocktail (TFA/EDT/Thioanisole/TIS/H$_2$O=90/2.5/2.5/2.5/2.5) ((TFA=trifluoroacetic acid; EDT=1,2-ethanedithiol; TIS=triisopropylsilane) was added to remove the protecting group of the peptide residue and separate the peptide from the resin.

⑥ After adding cooling diethyl ether 10 times the amount of the separated peptide in step ⑤ to precipitate the peptide, the resulting solution was centrifuged at 3000 rpm for 10 minutes to discard the clarified liquid, and then cooling diethyl ether was further added twice and centrifuged to obtain the peptide, and then the resulting peptide was purified with Prep-HPLC and freeze-dried.

<Preparation Example 4> Preparation of FKIGRL

FKIGRL was synthesized and prepared by coupling one by one from the end of the carboxyl group using the Fmoc solid phase peptide synthesis (SPPS) method. In other words, ① NH$_2$-Leu-2-chloro-trityl resin, in which leucine is attached to resin, was used.

② All amino acid raw materials used for peptide synthesis have the amino group end protected by Fmoc, and those (Fmoc-Phe-OH, Fmoc-Lys-OH, Fmoc-Ile-OH, Fmoc-Gly-OH, Fmoc-Arg(Pbf)-OH, etc.) protected by Trt, Boc, t-Bu, etc., which are all removed from acid (TFA, Trifluoroacetic acid), were used for residues.

③ For coupling, the protected amino acid and a coupling reagent HBTU/HOBt/NMM ((HBTU=2-(1H-benzotriazole-1-yl)-1,1,3,3-tetamethylaminium hexafluorophosphate; HOBt=N-Hydroxxybenzotriazole; NMM=4-Methylmorpholine) were dissolved in DMF, added to the prepared NH$_2$-leu-2-chloro-trityl resin, and reacted for two hours. After the reaction, the resin was washed in the order of DMF, MeOH, and DMF.

④ To remove Fmoc, 20% piperidine dissolved in DMF was added and reacted twice for 5 minutes at room temperature. After the reaction, the resin was washed in the order of DMF, MeOH, and DMF.

⑤ By repeating each of the above steps, the peptide base skeleton (NH$_2$-Phe-Lys-Ile-Gly-Arg-Leu-2-chloro-trityl resin) was made, after which cleavage cocktail (TFA/EDT/Thioanisole/TIS/H$_2$O=90/2.5/2.5/2.5/2.5) ((TFA=trifluoroacetic acid; EDT=1,2-ethanedithiol; TIS=triisopropylsilane) was added to remove the protecting group of the peptide residue and separate the peptide from the resin.

⑥ After adding cooling diethyl ether 10 times the amount of the separated peptide in step ⑤ to precipitate the peptide, the resulting solution was centrifuged at 3000 rpm for 10 minutes to discard the clarified liquid, and then cooling diethyl ether was further added twice and centrifuged to obtain the peptide, and then the resulting peptide was purified with Prep-HPLC and freeze-dried.

<Example 1> Synthesis of FX$_1$IGRL-NH$_2$(X$_1$=Dap(N$_3$))

The above modified peptide was prepared in such a way that —OH of the carboxyl group —COOH at the end of L of FX$_1$IGRL is substituted with —NH$_2$. In the preparation method, ① NH$_2$-Leu-MBHA link amide resin, in which leucine is attached to resin, was used.

② All amino acid raw materials used for peptide synthesis have the amino group end protected by Fmoc, and those (Fmoc-Phe-OH, Fmoc-Dap(N$_3$)—OH, Fmoc-Ile-OH, Fmoc-Gly-OH, Fmoc-Arg(Pbf)-OH, etc.) protected by Trt, Boc, t-Bu, etc., which are all removed from acid (TFA, Trifluoroacetic acid), were used for residues.

③ For coupling, the protected amino acids and a coupling reagent HBTU/HOBt/NMM were dissolved in DMF, added to the prepared NH$_2$-Leu-MBHA link amide resin, and then reacted for two hours. After the reaction, the resin was washed in the order of DMF, MeOH, and DMF.

④ To remove Fmoc, 20% piperidine dissolved in DMF was added and reacted twice for 5 minutes at room temperature. After the reaction, the resin was washed in the order of DMF, MeOH, and DMF.

⑤ By repeating the above steps, cleavage cocktail (TFA/EDT/Thioanisole/TIS/H$_2$O=90/2.5/2.5/2.5/2.5) was added to the peptide base skeleton (NH$_2$-Phe-Dap(N$_3$)—Ile-Gly-Arg-Leu-MBHA link amide resin) so as to remove the protecting group of the peptide residue and separate the peptide from the resin.

⑥ After adding cooling diethyl ether 10 times the amount of the separated peptide in step ⑤ to precipitate the peptide, the resulting solution was centrifuged at 3000 rpm for 10 minutes to discard the clarified liquid, and then cooling diethyl ether was further added twice and centrifuged to obtain the peptide, and then the resulting peptide was purified with Prep-HPLC and freeze-dried.

<Example 2> Synthesis of FX$_1$IGRL-OH (X$_1$=Dap(N$_3$))

FX$_1$IGRL was synthesized and prepared by coupling one by one from the end of the carboxyl group using the Fmoc solid phase peptide synthesis (SPPS) method. In other words, ① NH$_2$-Leu-2-chloro-trityl resin, in which leucine is attached to resin, was used.

② All amino acid raw materials used for peptide synthesis have the amino group end protected by Fmoc, and those (Fmoc-Phe-OH, Fmoc-Dap(N$_3$)—OH, Fmoc-Ile-OH, Fmoc-Gly-OH, Fmoc-Arg(Pbf)-OH, etc.) protected by Trt, Boc, t-Bu, etc., which are all removed from acid (TFA, Trifluoroacetic acid), were used for residues.

③ For coupling, the protected amino acids and a coupling reagent HBTU/HOBt/NMM ((HBTU=2-(1H-benzotriazole-1-yl)-1,1,3,3-tetamethylaminium hexafluorophosphate; HOBt=N-hydroxxybenzotriazole; NMM=4-methylmorpholine) were dissolved in DMF, added to the prepared NH$_2$-leu-2-chloro-trityl resin, and reacted for two hours. After the reaction, the resin was washed in the order of DMF, MeOH, and DMF.

④ To remove Fmoc, 20% piperidine dissolved in DMF was added and reacted twice for 5 minutes at room temperature. After the reaction, the resin was washed in the order of DMF, MeOH, and DMF.

⑤ By repeating each of the above steps, the peptide base skeleton (NH$_2$-Phe-Dap(N$_3$)—Ile-Gly-Arg-Leu-2-chlorotrityl resin) was made, after which cleavage cocktail (TFA/EDT/Thioanisole/TIS/H$_2$O=90/2.5/2.5/2.5/2.5) ((TFA=trifluoroacetic acid; EDT=1,2-ethanedithiol; TIS=triisopropylsilane) was added to remove the protecting group of the peptide residue and separate the peptide from the resin.

⑥ After adding cooling diethyl ether 10 times the amount of the separated peptide in step ⑤ to precipitate the peptide, the resulting solution was centrifuged at 3000 rpm for 10 minutes to discard the clarified liquid, and then cooling diethyl ether was further added twice and centrifuged to obtain the peptide, and then the resulting peptide was purified with Prep-HPLC and freeze-dried.

<Example 3> Synthesis of FCIGRL-NH$_2$ Dimer

A dimer was prepared by a disulfide-bond of respective cysteins, in which two peptides of FCIGRL-NH$_2$ prepared according to Preparation Example 1 are included in a peptide, and a specific method is as follows.

1. Preparation Method

Step 1) Removing of Resin Swelling & Fmoc

Rink amide MBHA resin was added to DCM, swelled for 30 minutes, and drained, after which 20% piperidine/DMF solution was added to the resin, stirred twice, and the resin was washed six times with DMF.

Step 2) Binding of Fmoc-A.A-OH

Fmoc-AA-OH was dissolved in DMF and added into a reactor with resin, after which 0.4M HBTU was added and stirred for one hour, and drained. Then, the resin was washed twice in DMF, and a 20% piperidine/DMF solution was added thereto, and stirred (2.5 min×2) twice. Then, the resin was washed six times with DMF. The process of step 2) was repeated for each amino acid (synthesizer: Symphony®X peptide synthesizer).

Step 3) Cleavage

Resin was added to the reactor, and trifluoroacetic acid/thioanisole/H$_2$O/1,2-ethandithiol (87.5%/5.0%/5.0%%/2.5%) was added thereto, and stirred for three hours. Then, the filtered cleavage solution was slowly added to cold ether to precipitate crystals and then dried.

Step 4) Dimer Reaction

After dissolving Linear in H$_2$O/ACN (acetonitrile) (1:1), 0.1M NH$_4$HCO$_3$ was added and done overnight at room temperature. After the reaction was completed, the resulting product was vacuum-dried.

2. Purification Method

The dimer prepared by the above method was purified using an HPLC instrument and conditions are as follows.

Test Solution:

K191009: Dissolve precisely weighed 1200 μmole of crude sample in 400.0 mL 20% ACN 1) HPLC System Model: Shimadzu HPLC Column: SHISEIDO, CAPCELL PAK C18 MGII 100 Å 5 um (30×250 mm)

Flow Rate 14 ml/min

Detector: spectrophotometer at 230 nm

Run time: 45 min

Oven Temp.: 35° C.

2) Purification of TFA Salt

Buffer: 0.05% TFA Water (A), 0.05% TFA acetonitrile (B)

Dissolve Condition: 100 mg/10 ml in water

Injection Volume: 4 ml

Gradient: 10-60%/50 min

<Example 4> Synthesis of FCIGRL-OH Dimer

A dimer of FCIGRL-OH was prepared by the same method as in Example 3, except that FCIGRL-OH of Preparation Example 2 was used instead of FCIGRL-NH$_2$ of Preparation Example 1.

<Example 5> Synthesis of X$_1$FCIGRL-NH$_2$ Dimer

1. Preparation Method

Step 1) Removing of Resin Swelling & Fmoc

Rink amide MBHA resin was added to DCM, swelled for 30 minutes, and drained, after which 20% piperidine/DMF solution was added to the resin, and stirred twice. Then, the resin was washed six times with DMF.

Step 2) Binding of Fmoc-A.A-OH

Fmoc-AA-OH was dissolved in DMF and added into a reactor with resin, after which 0.4M HBTU was added and stirred for one hour, and drained. Then, the resin was washed twice with DMF. Then, 20% piperidine/DMF solution was added and stirred twice (2.5 min×2), and then the resin was washed six times with DMF. The process of step 2) was repeated for each amino acid (synthesizer: Symphony®X peptide synthesizer).

Step 3) Dap(N$_3$) Coupling

Fmoc-Dap(N$_3$)—OH was dissolved in DMF and added into a reactor with resin, after which DIC(N,N'-diisopropylcarbodiimide)/HOBt(hydroxybenzotriazole)/DMF was added and then done overnight. Then, the resin was washed twice with DMF, and a 20% piperidine/DMF solution was added to the resin and stirred twice. Then, the resin was washed six times with DMF.

Step 4) Cleavage

Resin was added to the reactor, and trifluoroacetic acid/thioanisole/H$_2$O/1,2-ethandithiol (87.5%/5.0%/5.0%%/2.5%) was added thereto, and stirred for three hours. Then, the filtered cleavage solution was slowly added to cold ether to precipitate crystals and then dried.

Step 5) Dimer Reaction

DPDS(2,2'-dipyriyl disulfide, 0.24 eq)/MeOH solution was added to the solution of Linear/H$_2$O/CAN (4:1) and reacted for one hour. If linear remained, DPDS (0.05 eq) was added and further reacted for one hour, and then purified after completion of the reaction.

2. Purification Method

The dimer prepared by the above method was purified using an HPLC instrument and conditions are as follows.

Test Solution:

K191012: Dissolve precisely weighed 600 μmole of crude sample in 400.0 mL 20% ACN 1) HPLC System Model: Shimadzu HPLC Column: SHISEIDO, CAPCELL PAK C18 MGII 100 Å 5 um (30×250 mm)

Flow Rate 14 ml/min

Detector: spectrophotometer at 230 nm

Run time: 45 min

Oven Temp.: 35° C.

2) Purification of TFA Salt
  Buffer: 0.05% TFA Water (A), 0.05% TFA Acetonitrile (B)
  Dissolve Condition: 50 mg/10 ml in Water
  Injection Volume: 4 ml
  Gradient: 10-60%/50 min <Experimental Example 1> Identification of the Effect of Peptide and Peptide Dimer on Nasal Mucosal Administration (Fexofenadine)

1. Preparation of Experimental Animal

Male Sprague-Dawley (SD) rats (280-300 g) were acclimated for a minimum of two days in individual cages in a laboratory animal room. At this time, the rats were allowed to freely consume food and water before an experiment, provided with light for 12 hours, and maintained in the dark state for 12 hours. One day before the experiment, the animals were provided only with water and fasted.

2. Preparation of Test Substance

Each of the groups with the formulations including the peptide of above Preparation Example or above Example and fexofenadine HCl (BCS Class III) was prepared.

For a first group, a 5% (w/v) dextrose aqueous solution including fexofenadine and FCIGRL-NH$_2$ peptide dimer of Example 3 was prepared.

For a second group, a 5% (w/v) dextrose aqueous solution including fexofenadine and FCIGRL-OH peptide dimer of Example 4 was prepared.

For a third group, a 5% (w/v) dextrose aqueous solution including fexofenadine and FX$_1$IGRL-NH$_2$ (X=Dap(N$_3$)) peptide of Example 1 was prepared.

For a fourth group, a 5% (w/v) dextrose aqueous solution including fexofenadine and FX$_1$IGRL-OH of Example 2 was prepared.

For a fifth group, a 5% (w/v) dextrose aqueous solution including fexofenadine and FCIGRL-NH$_2$ of Preparation Example 1 was prepared.

For a sixth group, a 5% (w/v) dextrose aqueous solution including fexofenadine and FCIGRL-OH of Preparation Example 2 was prepared.

For a seventh group, a 5% (w/v) dextrose aqueous solution including fexofenadine and FRIGRL-OH of Preparation Example 3 was prepared.

For an eighth group, a 5% (w/v) dextrose aqueous solution including fexofenadine and FKIGRL-OH of Preparation Example 4 was prepared.

For a control group, a 5% (w/v) dextrose aqueous solution including fexofenadine only without the peptide was prepared.

3. Administration of Formulation Group

The rats prepared in above 1 were divided into each group of three to five rats so as to prepare a total of nine groups, after which each of the test substances prepared was intranasally administered into the group. At this time, the dosage of each drug was 1.0, 2.5 or 5.0 mg/kg per rat.

Before intranasal administration, the rat was anesthetized and cannulated into the femoral veno-artery using PE-50. The solution was carefully administered to the nostril of the rat using a micropipette (Eppendof) so as not to affect the nasal mucous membrane. At this time, the rat's body was laid on the floor and the head was placed while leaning against the wall.

4. Measurement of Fexofenadine Concentration

After administration of 1 mg/kg of the solution through a cannula inserted into the femoral vein of the rat, each 250 µl of blood was collected at 5, 10, 20, 30, 60, 120, and 240 minutes and saline was supplemented via the femoral artery. The collected blood was centrifuged at 13,000 rpm for 10 minutes so as to obtain 100 µl of plasma. After adding 200 µl of methanol to the obtained plasma, the resulting solution was subjected into vortex, and then centrifuged again at 13,000 rpm for 10 minutes to carry out deproteinization, and the supernatant was quantitatively analyzed by HPLC-MS.

FIG. 1 is a graph showing a fexofenadine blood concentration from rats in each group. Table 1 shows the pharmacokinetic parameters of fexofenadine, which are AUC, $C_{max}$ and $T_{max}$.

TABLE 1

| Fexofenadine (Mean ± SEM) | AUC$_{0-240\ min}$ (min µg/ml) | $C_{max}$ (ng/ml) | $T_{max}$ (min) |
|---|---|---|---|
| H-FCIGRL-NH$_2$ (Dimer) (Group 1) | 22.66 ± 4.40 (5.30-fold) | 528.07 ± 46.30 (9.76-fold) | 6.67 ± 1.67 (0.38-fold) |
| H-FCIGRL-OH (Dimer) (Group 2) | 15.56 ± 3.21 (3.64-fold) | 327.76 ± 78.20 (6.06-fold) | 7.24 ± 3.86 (0.41-fold) |
| H-FX$_1$IGRL-NH$_2$ X$_1$ = Dap(N$_3$) (Group 3) | 8.20 ± 1.49 (1.92-fold) | 157.13 ± 12.36 (2.90-fold) | 10.00 ± 0.00 (0.57-fold) |
| H-FX$_1$IGRL-OH X$_1$ = Dap(N$_3$) (Group 4) | 8.05 ± 1.12 (1.88-fold) | 106.47 ± 17.71 (1.97-fold) | 11.67 ± 3.65 (0.67-fold) |
| H-FCIGRL-NH$_2$ (Group 5) | 7.27 ± 1.36 (1.70-fold) | 78.69 ± 19.61 (1.45-fold) | 20.00 ± 5.77 (1.14-fold) |
| H-FCIGRL-OH (Group 6) | 6.53 ± 0.81 (1.53-fold) | 62.94 ± 9.49 (1.16-fold) | 26.67 ± 3.33 (1.52-fold) |
| H-FRIGRL-OH (Group 7) | 5.93 ± 0.53 (1.39-fold) | 39.59 ± 3.62 (0.73-fold) | 30.00 ± 0.00 (1.71-fold) |
| H-FKIGRL-OH (Group 8) | 4.65 ± 0.92 (1.09-fold) | 38.58 ± 0.21 (0.71-fold) | 20.00 ± 0.00 (1.14-fold) |
| Control group | 4.28 ± 0.39 | 54.11 ± 3.19 | 17.50 ± 2.50 |

As understood from the above table, it could be confirmed that groups dosed with fexofenadine and the peptide dimer of Example 3 (Group 1); and fexofenadine and the peptide dimer of Example 4 (Group 2) have AUC$_{0-360min}$ of fexofenadine 5.3 and 3.6 times remarkably higher than that of the group dosed with fexofenadine alone, respectively, and $C_{max}$ is remarkably and significantly increased 9.7 times and 6 times, respectively.

In addition, it could be confirmed that groups dosed with fexofenadine and the peptide of Example 1 (Group 3); and fexofenadine and the peptide of Example 2 (Group 4) have AUC$_{0-360min}$ of fexofenadine 2 and 1.9 times significantly higher than that of the group dosed with fexofenadine alone, respectively, and $C_{max}$ is remarkably and significantly increased 3 times and double, respectively.

Accordingly, it can be understood that a dimer of H—FX$_1$IGRL-NH$_2$ (X$_1$=Dap(N$_3$)) or H—FCIGRL-OH, which is a peptide including an amino acid sequence containing N$_3$ group according to the present invention, or a dimer of H—FCIGRL-NH$_2$ which is a peptide having OH of —COOH substituted with (transformed into) —NH$_2$ controls a tight junction in the nasal mucous membrane to remarkably promote the absorption of fexofenadine, which is a marker for drug absorption, thereby facilitating mucosal absorption of other active substances and improving bioavailability.

Figure 2:
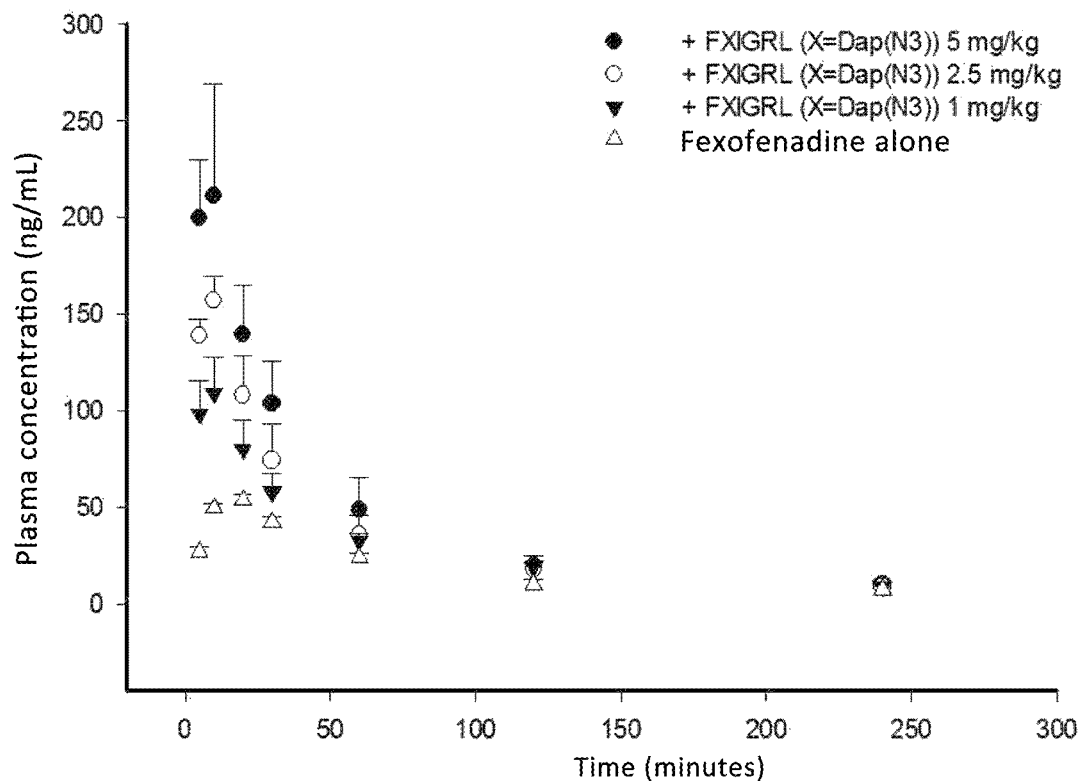
FIG. 2 is a time-concentration graph for confirming the degree of absorption in the nasal mucous membrane according to a dosage of the composition including a peptide of Example 1 of the present invention.

In addition, following table 2 shows that pharmacokinetic parameters of fexofenadine in each group according to a dosage of the peptide of Example 1 are indicated as AUC, $C_{max}$ and $T_{max}$, and FIG. 2 is a graph showing a fexofenadine blood concentration from rats in each group according to the dosage of the peptide of Example 1.

TABLE 2

| Fexofenadine (Mean ± SEM) | $AUC_{0-240\ min}$ (min ng/ml) | $C_{max}$ (pg/ml) | $T_{max}$ (min) |
| --- | --- | --- | --- |
| H-FX$_1$IGRL-NH$_2$ X$_1$ = Dap(N$_3$) 5 mg/kg (Group 8) | 10.63 ± 2.60 (2.48-fold) | 219.36 ± 49.89 (4.05-fold) | 7.50 ± 2.50 (0.43-fold) |
| H-FX$_1$IGRL-NH$_2$ X$_1$ = Dap(N$_3$) 2.5 mg/kg (Group 9) | 8.20 ± 1.49 (1.92-fold) | 157.13 ± 12.36 (2.90-fold) | 10.00 ± 0.00 (0.57-fold) |
| H-FX$_1$IGRL-NH$_2$ X$_1$ = Dap(N$_3$) 1 mg/kg (Group 10) | 7.03 ± 0.67 (1.64-fold) | 108.89 ± 18.74 (2.01-fold) | 10.00 ± 0.00 (0.57-fold) |
| Control group | 4.28 ± 0.39 | 54.11 ± 3.19 | 17.50 ± 2.50 |

As understood from above table 2 and FIG. 2, it could be confirmed that the group dosed with fexofenadine (1 mg/kg) and 5 mg/kg of peptide of Example 1 (Group 8); the group dosed with fexofenadine (1 mg/kg) and 2.5 mg/kg of peptide of Example 1 (Group 9); and the group dosed with fexofenadine (1 mg/kg) and 1 mg/kg of peptide of Example 1 (Group 10) have $AUC_{0-360min}$ of fexofenadine about 2.5, 2 and 1.6 times remarkably higher than that of the group dosed with fexofenadine (1 mg/kg) alone, respectively, and $C_{max}$ is remarkably and significantly increased 4, 3 and 2 times, respectively, with a remarkable effect of peptide on promoting permeation.

5. Analysis of Drug Permeability

The permeability of various drugs was confirmed through the Caco-2 monolayer and its specific experiment method was performed with reference to Effect of the six-mer synthetic peptide (AT$_{1002}$) fragment of zonula occludens toxin on the intestinal absorption of cyclosporin A (International Journal of Pharmaceutics 351 (2008) 8-14). An experiment on the permeability was conducted after confirming the degree of cell culture through the Papp value (3.89×10$^{-5}$ cm/sec) of metoprolol.

TABLE 3

| Peptide Drug | Control group | FCIGRL-NH$_2$ (Preparation Example 1) | H-FCIGRL-NH$_2$ (Dimer) (Example 3) | H-FXIGRL-NH$_2$ X = Dap(N$_3$) (Example 1) |
| --- | --- | --- | --- | --- |
| Fexofenadine | 1.00 | 1.16 ± 0.33 | 22.18 ± 3.88 | 22.16 ± 3.57 |
| Cyclophosphorin A | 1.00 | 1.23 ± 0.11 | 17.35 ± 4.26 | 16.28 ± 2.95 |
| Acyclovir | 1.00 | 1.05 ± 0.23 | 15.27 ± 3.21 | 15.82 ± 2.72 |
| Docetaxel | 1.00 | 1.08 ± 0.07 | 12.30 ± 2.95 | 11.62 ± 3.19 |
| Doxorubicin | 1.00 | 1.25 ± 0.32 | 16.82 ± 3.67 | 14.26 ± 4.25 |
| Leuprorelin | 1.00 | 1.01 ± 0.12 | 8.23 ± 2.56 | 7.35 ± 1.68 |
| Exedin | 1.00 | 1.21 ± 0.27 | 7.38 ± 2.61 | 7.21 ± 2.12 |
| Mannitol | 1.00 | 1.31 ± 0.30 | 20.35 ± 3.56 | 19.26 ± 2.94 |
| Atenolol | 1.00 | 1.12 ± 0.19 | 12.38 ± 1.32 | 12.75 ± 1.72 |
| Rutin | 1.00 | 1.53 ± 0.17 | 15.19 ± 1.86 | 8.7 ± 1.39 |

As shown in above Table 3, as a result of obtaining an increase rate of Papp (cm/sec) of each drug by each peptide (5 mM) through an experiment on permeability, it could be confirmed that the peptide dimer of Example 3 (H—FCIGRL-NH$_2$) and the peptide of Example 1 (H—FX$_1$IGRL-NH$_2$, X$_1$=Dap(N$_3$)) show a remarkably excellent effect of promoting mucous membrane permeation, which is at least seven times higher.

<Experimental Example 2> Identification of the Effect of Peptide and Peptide Dimer on Intestinal Mucosal Administration (Exenadine)

1. Preparation of Experimental Animal and Test Substance

A method for preparing experimental animals was the same as shown in above Experimental Example 1. For a test substance, 0.5% (w/v) levan aqueous solution including exenadine and FCIGRL-NH$_2$ peptide dimer of Example 3 was prepared as an experimental group, and 0.5% (w/v) levan aqueous solution including exenadine without peptide was prepared as a control group.

2. Administration of Formulation Group

The rats prepared according to the method of above Experimental Example 1 were divided into each group of three to five rats so as to prepare a total of three groups, after which the test substance prepared was intestinally (duodenum) administered into the group.

Before drug administration, the rat was anesthetized and cannulated into the femoral veno-artery using PE-50. An abdominal cavity was opened and the test substance was administered to an upper duodenum of the small intestine.

3. Measurement of Exenadine Blood Concentration

After administration of the solution through a cannula inserted into the femoral vein of the rat, each 250 μl of blood was collected at 5, 10, 20, 40, 60, 120, 180 and 240 minutes and saline was supplemented via the femoral artery. The collected blood was centrifuged at 13,000 rpm for 10 minutes so as to obtain 100 μl of plasma. After adding 200 μl of methanol to the obtained plasma, the resulting solution was subjected into vortex, and then centrifuged again at 13,000 rpm for 10 minutes to carry out deproteinization, and the supernatant was quantitatively analyzed by HPLC-MS.

Figure 3:
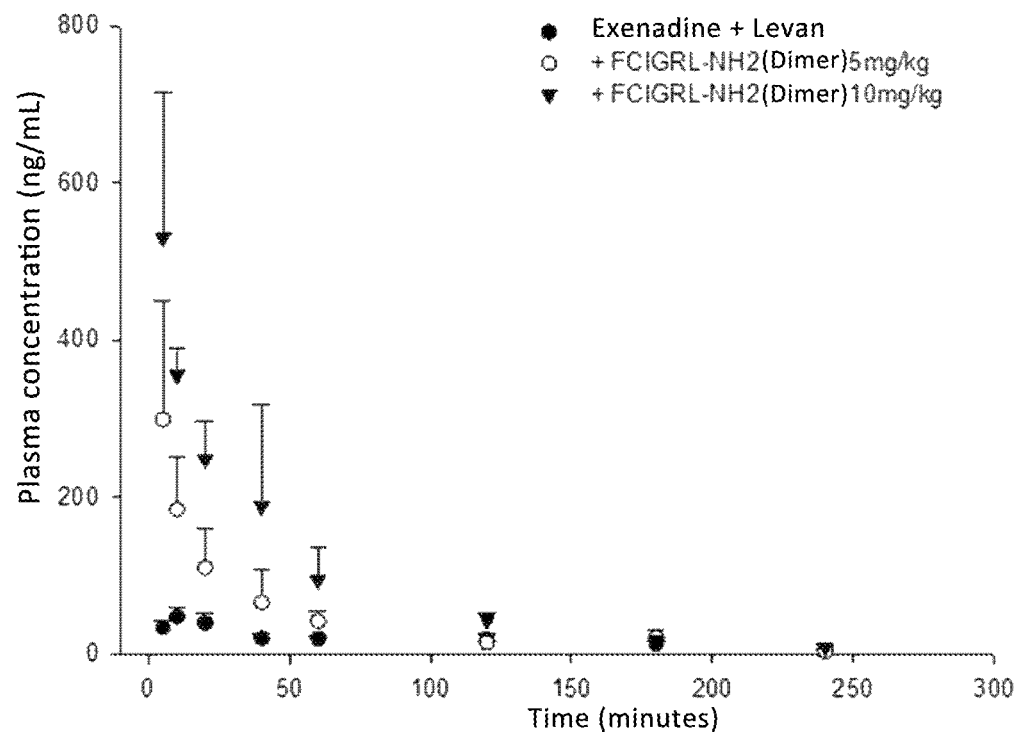
FIG. 3 is a time-concentration graph for confirming the degree of absorption of exenadine in the intestinal mucous membrane with regard to the composition including a peptide dimer prepared according to Example 3 of the present invention.

A graph of exenadine blood concentration of each group rat is shown in FIG. 3, and following table 4 shows the AUC value of exenadine.

TABLE 4

| Exenadine | H-FCIGRL-NH$_2$ (Dimer) | | |
| --- | --- | --- | --- |
| (Mean ± SEM) | None (Control) | 5 mg/kg | 10 mg/kg |
| $AUC_{0-240\ min}$ (min μg/mL) | 4.49 ± 0.94 | 9.77 ± 3.88(2.17-fold) | 20.56 ± 6.32 (4.57-fold) |

As understood from above table 4 and FIG. 3 below, it could be confirmed that the group dosed with exenadine (10 mg/kg) and 5 mg/kg of H—FCIGRL-NH$_2$ dimer of Example 3 and the group dosed with exenadine (10 mg/kg) and 10 mg/kg of H—FCIGRL-NH$_2$ dimer of Example 3 have AUC about 2.17 and 4.57 times remarkably higher than that of the (control) group dosed with exenadine (10 mg/kg) alone. Accordingly, it can be understood that the H—FCIGRL-NH$_2$ dimer controls a tight junction in intestinal mucous membrane to remarkably promote the absorption of exenadine, a marker of drug absorption, suggesting that the peptide dimer of the present invention promotes mucosal absorption of other active substances so as to improve bioavailability.

<Experimental Example 3> Identification of the Effect of Peptide and Peptide Dimer on Intestinal Mucosal Administration (Doxorubicin)

1. Preparation of Experimental Animal and Test Substance

A method for preparing experimental animals was the same as shown in above Experimental Example 1.

For a test substance, a 0.5% (w/v) levan aqueous solution including doxorubicin and FCIGRL-NH$_2$ of Preparation Example 1 was prepared as a first group.

For a second group, a 0.5% (w/v) levan aqueous solution including doxorubicin and FX$_1$IGRL-NH$_2$ (X=Dap(N$_3$)) peptide of Example 1 was prepared.

For a third group, a 0.5% (w/v) levan aqueous solution including doxorubicin and X$_1$FCIGRL-NH$_2$ peptide dimer of Example 5 was prepared.

For a fourth group, a 0.5% (w/v) levan aqueous solution including doxorubicin and FCIGRL-NH$_2$ peptide dimer of Example 3 was prepared.

For a control group, a 0.5% (w/v) levan aqueous solution including doxorubicin without the peptide was prepared.

2. Administration of Formulation Group

The rats prepared according to the method of above Experimental Example 1 were divided into each group of three to five rats so as to prepare a total of five groups, after which a test substance prepared was intestinally (duodenum) administered into the group. At this time, the dosage of peptide-containing drug was 10 mg/kg for each group.

Before drug administration, the rat was anesthetized and cannulated into the femoral veno-artery using PE-50. An abdominal cavity was opened and the test substance was administered to an upper duodenum of the small intestine.

3. Measurement of Doxorubicin Blood Concentration

After administration of the solution through a cannula inserted into the femoral vein of the rat, each 250 µl of blood was collected at 5, 10, 20, 40, 60, 120, 180 and 240 minutes and saline was supplemented via the femoral artery. The collected blood was centrifuged at 13,000 rpm for 10 minutes so as to obtain 100 µl of plasma. After adding 200 µl of methanol to the obtained plasma, the resulting solution was subjected into vortex, and then centrifuged again at 13,000 rpm for 10 minutes to carry out deproteinization, and the supernatant was quantitatively analyzed by HPLC-Fluorescence.

Figure 4:
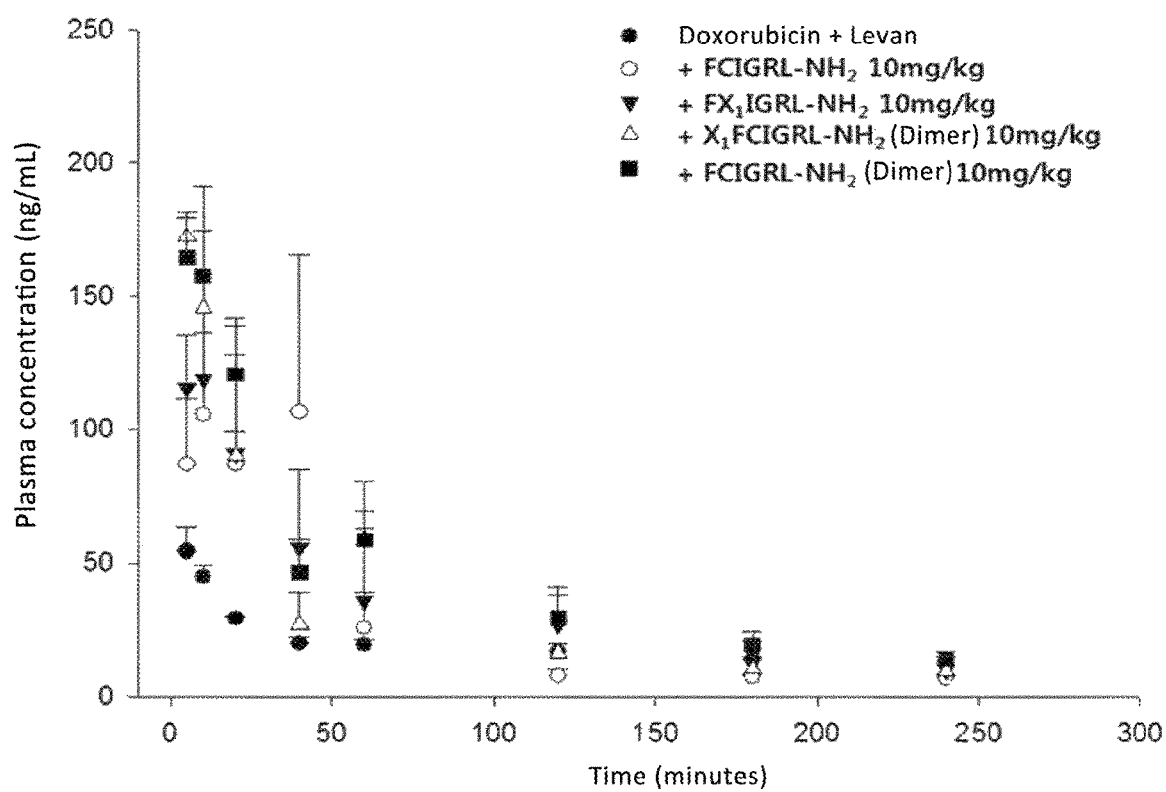
FIG. 4 is a time-concentration graph for confirming the degree of absorption of doxorubicin in the intestinal mucous membrane with regard to the composition including peptides or peptide dimers prepared according to Preparation Example 1, Example 1, 3 or 5 of the present invention.

A graph of doxorubicin blood concentration of each group rat is shown in FIG. 4, and following table 5 shows the AUC value of doxorubicin.

TABLE 5

| Mean ± SEM | Doxorubicin (Control) | H-FCIGRL-NH$_2$ 10 mg/kg (Group 1) | FX$_1$IGRL-NH$_2$ 10 mg/kg (Group 2) | X$_1$FCIGRL-NH$_2$(Dimer) 10 mg/kg (Group 3) | H-FCIGRL-NH$_2$ (Dimer) 10 mg/kg (Group 4) |
|---|---|---|---|---|---|
| AUC$_{0-240\ min}$ (min µg/mL) | 4.57 ± 0.24 | 6.79 ± 1.29 (1.49-fold) | 8.26 ± 0.94 (1.81-fold) | 8.06 ± 1.43 (1.77-fold) | 10.44 ± 1.77 (2.29-fold) |

As understood from above table 5 and FIG. 4 below, it could be confirmed that all the groups dosed with the drugs containing the peptide or the peptide dimer and doxorubicin have AUC values higher than that of the control group dosed with doxorubicin only. Accordingly, it can be understood that the peptide and the peptide dimer control a tight junction in intestinal mucous membrane to remarkably promote the absorption of doxorubicin, a marker of drug absorption, suggesting that the peptide dimer of the present invention promotes mucosal absorption of other active substances so as to improve bioavailability.

While specific portions of the present invention have been described in detail above, it is apparent to those having ordinary skill in the art that such detailed descriptions are set forth to illustrate exemplary embodiments only, but are not construed to limit the scope of the present invention. Thus, it should be understood that the substantial scope of the present invention is defined by the accompanying claims and equivalents thereto.

INDUSTRIAL APPLICABILITY

A peptide or a peptide multimer according to the present invention serves to control a tight junction between cells, so as to improve mucosal permeability, thereby facilitating the absorption, through a mucous membrane, of an active ingredient of co-administered drugs and the like. Thus, the bioavailability of the active ingredient can be significantly improved, and as a result, the therapeutic effect of the active ingredient can be significantly improved.

The invention claimed is:

1. A method for promoting mucous membrane permeation of an active ingredient, the method comprising a step of administering a composition together with the active ingredient to a subject, wherein the composition comprises at least one peptide selected from the group consisting of: a peptide comprising an amino acid sequence represented by SEQ ID NO: 1; a peptide comprising an amino acid sequence represented by SEQ ID NO: 2; a peptide comprising an amino acid sequence represented by SEQ ID NO: 3; a peptide comprising an amino acid sequence represented by SEQ ID NO: 4; a peptide comprising an amino acid sequence represented by SEQ ID NO: 5; a peptide comprising an amino acid sequence represented by SEQ ID NO: 12; a peptide comprising an amino acid sequence represented by SEQ ID NO: 14; and a peptide comprising an amino acid sequence represented by SEQ ID NO: 15.

2. The method of claim 1, wherein the composition further comprises a pharmaceutically acceptable additive or adjuvant.

3. The method of claim 1, wherein the mucous membrane is a mucous membrane in which a tight junction is expressed.

4. The method of claim 3, wherein the mucous membrane is a mucous membrane of small intestine, nasal cavity, oral cavity, skin, lung, vagina, rectum or colon.

5. The method of claim 1, wherein the active ingredient is fexofenadine, cyclophosphorin A, acyclovir, docetaxel, doxorubicin, leuprorelin, exedin, mannitol, atenolol or rutin.

6. The method of claim 1, wherein the active ingredient is fexofenadine.

7. A formulation comprising at least one peptide selected from the group consisting of: a peptide comprising an amino acid sequence represented by SEQ ID NO: 1; a peptide comprising an amino acid sequence represented by SEQ ID NO: 2; a peptide comprising an amino acid sequence represented by SEQ ID NO: 3; a peptide comprising an amino acid sequence represented by SEQ ID NO: 4; a peptide comprising an amino acid sequence represented by SEQ ID NO: 5; and a peptide comprising an amino acid sequence represented by SEQ ID NO: 12; a peptide comprising an amino acid sequence represented by SEQ ID NO: 14; and a peptide comprising an amino acid sequence represented by SEQ ID NO: 15, and an active ingredient.

8. The formulation of claim 7, wherein the formulation is formulated for administering enterally, nasally, oromucosally, transdermally, transpulmonarily, rectally or vaginally.

9. The formulation of claim 7, wherein the formulation further comprises a pharmaceutically acceptable additive or adjuvant.

* * * * *